US012618850B2

(12) United States Patent
Daud et al.

(10) Patent No.: US 12,618,850 B2
(45) Date of Patent: May 5, 2026

(54) METHODS FOR ANALYZING AAV CAPSID PROTEINS

(71) Applicant: Sarepta Therapeutics, Inc., Cambridge, MA (US)

(72) Inventors: Kunal Daud, Cambridge, MA (US); Ju Li, Cambridge, MA (US); Uditha Dealwis, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 832 days.

(21) Appl. No.: 17/782,472

(22) PCT Filed: Dec. 30, 2020

(86) PCT No.: PCT/US2020/067395
§ 371 (c)(1),
(2) Date: Jun. 3, 2022

(87) PCT Pub. No.: WO2021/138381
PCT Pub. Date: Jul. 8, 2021

(65) Prior Publication Data
US 2023/0204595 A1 Jun. 29, 2023

Related U.S. Application Data

(60) Provisional application No. 63/119,909, filed on Dec. 1, 2020, provisional application No. 63/073,188, filed
(Continued)

(51) Int. Cl.
*G01N 33/68* (2006.01)
*C07K 14/005* (2006.01)
*G01N 30/88* (2006.01)

(52) U.S. Cl.
CPC ....... *G01N 33/6848* (2013.01); *C07K 14/005* (2013.01); *C12N 2750/14122* (2013.01); *G01N 2030/8831* (2013.01)

(58) Field of Classification Search
CPC ........ C07K 14/005; C12N 2750/14122; G01N 2030/8831; G01N 33/6848
See application file for complete search history.

(56) References Cited

U.S. PATENT DOCUMENTS

2008/0064856 A1* 3/2008 Warne .................. A61K 9/0019
530/383
2014/0323956 A1 10/2014 Mendell et al.
(Continued)

FOREIGN PATENT DOCUMENTS

WO WO-0183692 A2 11/2001
WO WO-2013158879 A1 10/2013
(Continued)

OTHER PUBLICATIONS

Palmer (Separate—Reverse-phase separation of proteins, peptide and other biomolecules). https://www.agilent.com/cs/library/eseminars/public/SEPARATE_Reverse-Phase_Separation_06Aug2008.pdf (Year: 2008).*
(Continued)

*Primary Examiner* — Jennifer Wecker
*Assistant Examiner* — Jonathan Bortoli
(74) *Attorney, Agent, or Firm* — STERNE, KESSLER, GOLDSTEIN & FOX P.L.L.C.

(57) ABSTRACT

Provided are methods to characterize the VP1, VP2 and VPS capsid proteins in an adeno-associated virus (AAV) particle using liquid chromatography mass spectrometry, and/or ultraviolet (UV)-visible spectroscopy. The methods generally include the steps of (a) subjecting an AAV particle to liquid chromatography to denature and then separate the VP1, VP2 and VPS capsid proteins, and (b) subjecting the separated VP1, VP2 and VPS capsid proteins produced in step (a) to UV and mass spectrometry to determine the ratio and masses of the VP1, VP2 and VPS capsid proteins in the AAV particle. In another aspect, the disclosure provides an
(Continued)

Response Units vs. Acquisition Time (min)

AAV composition comprising a post-translation modification. The disclosure also provides methods for characterizing the purity of AAV compositions using liquid chromatography mass spectrometry.

17 Claims, 11 Drawing Sheets

Specification includes a Sequence Listing.

Related U.S. Application Data on Sep. 1, 2020, provisional application No. 62/956,681, filed on Jan. 3, 2020.

(56)                 References Cited

U.S. PATENT DOCUMENTS

| | | | | |
|---|---|---|---|---|
| 2019/0161725 | A1 * | 5/2019 | Chen | C12N 7/00 |
| 2020/0131533 | A1 * | 4/2020 | Wang | C12N 15/86 |
| 2020/0407750 | A1 * | 12/2020 | Wilson | C12N 15/86 |

FOREIGN PATENT DOCUMENTS

| | | | | |
|---|---|---|---|---|
| WO | WO-2018035059 A1 * | 2/2018 | | C07K 14/005 |
| WO | WO-2019168961 A1 | 9/2019 | | |
| WO | WO-2019169004 A1 | 9/2019 | | |

OTHER PUBLICATIONS

Aucoin, M., et al., "Critical assessment of current adeno-associated viral vector production and quantification methods," Biotechnol. Adv. 26(1):73-88, Elsevier, Netherlands (2008).

Bark, S.J., et al., "High-temperature protein mass mapping using a thermophilic protease," J. Am. Chem. Soc. 123(8):1774-1775, American Chemical Society, United States (2001).

Bauer, D.W., et al., "Exploring the Balance between DNA Pressure and Capsid Stability in Herpesviruses and Phages," J. Virol. 9288-9298, American Society for Microbiology, United States (2015).

Bosma, B., et al., "Optimization of viral protein ratios for production of rAAV serotype 5 in the baculovirus system," Gene Ther. 25(6):415-424, Nature Publishing Group, United Kingdom (2018).

Buller, R.M. and Rose, J.A., "Characterization of adenovirus-associated virus-induced polypeptides in KB cells," J. Virol. 25:331-338, American Society for Microbiology, United States (1978).

Giles, A.R., et al., "Deamidation of Amino Acids on the Surface of Adeno-Associated Virus Capsids Leads to Charge Heterogeneity and Altered Vector Function," Mol. Ther. 26(12):2848-2862, Cell Press, United States (2018).

International Search Report and Written Opinion for International Application No. PCT/US2020/067395, European Patent Office, Netherlands, mailed on Sep. 6, 2021, 20 pages.

Jin, X., et al., "Direct Liquid Chromatography/Mass Spectrometry Analysis for Complete Characterization of Recombinant Adeno-Associated Virus Capsid Proteins," Hum. Gene Ther. Methods 28(5):255-267, with Supplemental Data, Mary Ann Liebert, Inc., United States (2017).

Johnson, F.B., et al., "Structural proteins of adenovirus-associated virus type 3," J. Virol. 8(6):860-863, American Society for Microbiology, United States (1971).

Marsic, et al., "Vector design Tour de Force: integrating combinatorial and rational approaches to derive novel adeno-associated virus variants," Mol. Ther. 22(11):1900-1909, Cell Press, United States (2014).

Rayaprolu, V., et al., "Comparative analysis of adeno-associated virus capsid stability and dynamics," J. Virol. 13150-13160, American Society for Microbiology, United States (2013).

Van Vliet, K., et al., "Adeno-associated virus capsid serotype identification: Analytical methods development and application," J. Virol. Methods 159(2):167-177, Elsevier, Netherlands (2009).

Yang, Y., "High-Temperature Liquid Chromatography," LCGC Supplements, accessed at https://www.chromatographyonline.com/view/high-temperature-liquid-chromatography, Apr. 1, 2008, 9 pages.

Guan, Z., et al., "Detection and Characterization of Methionine Oxidation in Peptides by Collision-Induced Dissociation and Electron Capture Dissociation," J Am Soc Mass Spectrom 14(6):605-613, Elsevier, Netherlands (2003).

Fekete, S., et al., "Impact of mobile phase temperature on recovery and stability of monoclonal antibodies using recent reversed-phase stationary phases," J Sep Sci 35(22):3113-3123, Wiley, United States (2012).

Dillon, T. M., et al., "Optimization of a reversed-phase high-performance liquid chromatography/mass spectrometry method for characterizing recombinant antibody heterogeneity and stability," Journal of Chromatography A, 1120(1-2):112-120, Elsevier, Netherlands (2006).

Menz, M., et al., "Influence of Column Temperature on Reversed-Phase Chromatography of an Intact Antibody," Thermo Scientific, Technical Note 173, Thermo Fisher Scientific, Inc., United States (2016).

* cited by examiner

Fig. 5

| Amino Acid Residue | Lot 1 | Lot 2 | Lot 3 | Lot 4 | Lot 5 | Lot 6 | Lot 7 | Lot 8 |
|---|---|---|---|---|---|---|---|---|
| N57 | 11.3 | 8.9 | 11.4 | 13.5 | 11.4 | 10.5 | 10.3 | 12.5 |
| N254/N255 | 1.6 | 1.3 | 3.3 | ND | ND | 1.5 | 3.4 | 3.6 |
| N63 | 10.9 | 12.4 | 19.1 | 9.2 | 12.7 | 7.5 | 7.0 | 7.9 |

| Amino Acid Residue | Lot 1 | Lot 2 | Lot 3 | Lot 4 | Lot 5 | Lot 6 | Lot 7 | Lot 8 |
|---|---|---|---|---|---|---|---|---|
| M437 | 0.5 | 0.4 | 0.5 | 0.3 | 0.5 | 0.4 | 0.4 | 0.4 |
| M473 | ND | 0.6 | ND | 0.8 | ND | ND | 0.8 | 0.7 |
| M526 | ND | 0.8 | 0.6 | 0.4 | 0.6 | 2.1 | 0.8 | 0.6 |
| M544 | 1.1 | 1.1 | 0.9 | 0.8 | 0.9 | 0.8 | 1.1 | 0.8 |
| M560 | ND | 0.7 | ND | 0.9 | 1.0 | 0.9 | 0.9 | 1.0 |
| M637 | 0.7 | 0.8 | 0.9 | 0.7 | 0.9 | 0.8 | 0.9 | 0.8 |

Fig. 6

METHODS FOR ANALYZING AAV CAPSID PROTEINS

CROSS REFERENCE TO RELATED APPLICATIONS

This application claims benefit under 35 U.S.C. § 119(e) of U.S. Provisional Application No. 62/956,681 filed Jan. 3, 2020, U.S. Provisional Application No. 63/073,188 filed Sep. 1, 2020, and U.S. Provisional Application No. 63/119, 909 filed Dec. 1, 2020, the contents of each of which are incorporated herein by reference in their entireties.

REFERENCE TO SEQ REFERENCE TO SEQUENCE LISTING SUBMITTED ELECTRONICALLY VIA EFS-WEB

The content of the electronically submitted sequence listing in ASCII text file (Name: 4140 0600003 Seqlisting ST25; Size: 1,978 bytes; and Date of Creation: Nov. 21, 2022) is herein incorporated by reference in its entirety.

TECHNICAL FIELD

The disclosure relates to methods for characterizing the VP1, VP2 and VP3 capsid proteins in an adeno-associated virus (AAV) particle and the purity of an AAV composition using liquid chromatography and mass spectrometry.

BACKGROUND

Adeno-Associated viruses (AAVs) are quickly becoming one of the most widely used vehicles for delivering gene therapy. The excellent safety profile along with the high efficiency of transduction of a broad range of target tissues has made AAV the most widely used platform for gene therapy. AAV is a small virus belonging to the Parvoviridae family. The virus is composed of a non-enveloped icosahedral capsid containing a linear single stranded DNA genome of about 4.7 kilobases. AAV is commonly expressed recombinantly in suitable host cells. However, recombinant AAV may be contaminated by proteins from the host cell lysate.

The AAV capsid includes a mixture of VP1, VP2 and VP3 proteins, which are produced from a single viral Cap gene by alternative splicing and translation, and which self-assemble to form the capsid. AAV capsid proteins play a critical role in viral infectivity, tissue tropism, and potency, and the ability to fully characterize the mass and ratios of capsid proteins is becoming increasingly important for the commercial manufacturing of AAV for gene therapy.

In particular, the stoichiometry of the VPs is crucial for infectivity of viral vectors. For example, high levels of VP3 capsid was negatively associated with poor transduction efficiency and reduced potency even when the VP1/VP2 ratio was not in balance. (Gene Therapy, volume 25, pages 415-424 (2018)). Since the ratio of structural proteins VP1, VP2, and VP3 from manufacture may fluctuate in a wide range, e.g., 1:1:5 to 1:1:20 (Biotechnol Adv., 26(1):73-88 (2008)), the accurate measurement of the ratio among the three capsid proteins is important in the AAV vector quality control. However, the current methods attempted to measure the masses of capsid proteins but failed to determine the stoichiometry of each of the VPs (WO 2018/035059). Thus, robust methods for a more accurate characterization of ratios and modifications of AAV capsid proteins and the purity of rAAV compositions is needed in the gene therapy industry.

SUMMARY

The disclosure provides methods to characterize the VP1, VP2 and VP3 capsid proteins in an adeno-associated virus (AAV) particle using liquid chromatography and mass spectrometry. The methods disclosed herein are used to determine the ratio of VP1, VP2 and VP3 capsid proteins in AAV particle, and/or the masses of one or more of the VP1, VP2 and VP3 capsid proteins.

In some aspects, the present disclosure provides a method to determine the ratio of VP1, VP2 and VP3 capsid proteins in an adeno-associated virus (AAV) particle. The method includes the steps of subjecting the AAV particle to a liquid chromatography at about 70° C. to about 90° C., wherein the masses and ratio of VP1, VP2 and VP3 capsid proteins is determined by mass spectrometry and/or ultraviolet (UV)-visible spectroscopy. In some aspects, the individual masses of the capsid proteins are measured by mass spectrometry. In some aspects, the capsids on the AAV particle is denatured into the individual VP1, VP2 and VP3 proteins in the column of the liquid chromatography. In some aspects, the capsid proteins are separated by the liquid chromatography.

In some aspects, the method further includes determining the masses of one or more of the VP1, VP2 and VP3 capsid proteins in the AAV particle using mass spectrometry.

In some aspects, the relative amounts of the VP1, VP2 and VP3 capsid proteins are determined by analyzing the ultraviolet (UV) chromatogram of the VP1, VP2 and VP3 capsid proteins. In some aspects the liquid chromatography is reverse phase liquid chromatography. In some aspects, the AAV particle is AAVrh74.

In some aspects, the chromatography uses a first mobile phase including trifluoroacetic acid in water. In some aspects, the chromatography uses a second mobile phase including trifluoroacetic acid in the mixture of acetonitrile and water. In some aspects, the percentage of the second mobile phase, in a combination of the first mobile phase and the second mobile phase, in the chromatography is increased over time.

In some aspects, the mass spectrometry comprises a fragmentor voltage of about 125-350 V.

Deamidation is one of the common Post-Translational modifications (PTM) observed in proteins that is known to have a significant impact on the activity and stability of proteins. Deamidation is usually caused by the hydrolysis of the amide side chain of Asparagine to form a mixture of aspartic and isoaspartic acid. In some aspects, the deamidation is the hydrolysis reaction of cytosine into uracil, releasing ammonia in the process. This can occur in vitro through the use of bisulfite, which deaminates cytosine, but not 5-methylcytosine. In some aspects, deamination of 5-methylcytosine results in thymine and ammonia. In some aspects, glutamine residues also undergo deamidation to form a mixture of glutamic and isoglutamic acid, however glutamine residues are significantly less susceptible to deamidation as compared to Asparagine. In some aspects, deamination of guanine results in the formation of xanthine. In some aspects, deamidation of adenine results in the formation of hypoxanthine. Deamidation of capsid proteins can impact the stability and activity of the AAV formulations.

In some aspects of the disclosure, mass spectrometry is used to study post-translational modifications like deamidation. In some aspects, the protein can be denatured using reagents like Guanidine and Urea. The denatured protein is reduced using 1,4-Dithiothreitol (DTT) or Tris(2-carboxyehtyl)phosphine (TECP) to break the disulfide linkages.

The reduced disulfide linkages are then alkylated using Iodoacetamide. The denaturation and alkylation steps are carried out to ensure that the protein is unfolded and therefore completely accessible to the proteases. The denatured and reduced protein is then digested using one of several proteases like Trypsin. The digested peptides are separated on a HPLC/UPLC using RP-HPLC. Separated peptides are then detected using their m/z ratios on the Mass Spectrometer, typically a Q-ToF or an Orbitrap. Using appropriate software and databases the peptides are identified. Deamidation is identified as an increase of approximately 1 Da as compared to the theoretical value of the peptide.

In some aspects, the method further includes determining post translational modification of at least one of VP1, VP2 and VP3 capsid proteins. In some aspects, the method further includes post translational phosphorylation or acetylation of at least one of VP1, VP2 and VP3 capsid proteins.

The disclosure also provides a method of characterizing host cell proteins in an AAV composition, comprising immunoprecipitating viral capsid proteins from the composition; digesting residual host cell proteins; and analyzing the digested proteins with liquid chromatography quadrupole time of flight mass spectrometry (LC-QTOF-MS) to identify host cell proteins.

In some aspects, the immunoprecipitation comprises incubating the AAV composition with an anti-AAV VP1 antibody, an anti-AAV VP2 antibody, an anti-AAV VP3 antibody, or combinations thereof In some aspects, the method further comprises analyzing the digested host cell proteins with iterative MS/MS.

In some aspects, the digestion is done in solution. In some aspects, the digestion is performed at a temperature of about 60° C. to about 80° C. In some aspects the digestion is performed at about 70° C.

In some aspects, the method further comprises spiking the AAV composition with a known amount of at least one known protein standard. In some aspects, the at least one known protein standard is a human or bovine protein standard. In some aspects, the method further comprises quantifying the amount of the digested host cell proteins relative to the at least one protein standard.

In some aspects, the liquid chromatography is a reverse phase liquid chromatography. In some aspects, the reverse phase liquid chromatography is performed using a C18 column, a C8 column, or a C4 column. In some aspects, the liquid chromatography is performed using a C8 column. In some aspects, the column comprises particles of about 1.2-3.5 μm. In some aspects, the column comprises particles of about 1.7 μm or about 1.8 μm. In some aspects, the column is from about 50 mm to about 300 mm long and has an internal diameter of from about 1 mm to about 4.6 mm. In some aspects, the column is about 150 mm long and has an internal diameter of about 2.1 mm.

In some aspects, the liquid chromatography is performed at about 40° C. to about 50° C. In some aspects, the liquid chromatography is performed at about 45° C.

In some aspects, the liquid chromatography comprises a first mobile phase that comprises formic acid. In some aspects, the first mobile phase comprises from about 0.05% to about 0.15% formic acid by volume. In some aspects, the first mobile phase comprises about 0.1% formic acid by volume.

In some aspects, the liquid chromatography comprises a second mobile phase that comprises formic acid in a mixture of acetonitrile and water. In some aspects, the second mobile phase comprises from about 0.05% to about 0.15% formic acid by volume. In some aspects, the second mobile phase comprises about 0.1% formic acid by volume. In some aspects, the second mobile phase comprises about 80-95% acetonitrile by volume. In some aspects, the second mobile phase comprises about 90% acetonitrile by volume and about 10% water by volume.

In some aspects, the percentage of the second mobile phase, as compared to a combination of the first mobile phase and the second mobile phase, in the liquid chromatography is increased over time. In some aspects, the percentage of the second mobile phase is increased from about 2% to about 50%. In some aspects, the percentage of the second mobile phase is increased from about 2% to about 50% by volume over about 120 minutes. In some aspects, the percentage of the second mobile phase is subsequently increased to 100% by volume over about 25 minutes. In some aspects, the percentage of the second mobile phase is subsequently maintained at 100% by volume for about one minute. In some aspects, the second mobile phase is subsequently decreased to about 2% by volume over about 4 minutes. In some aspects, the percentage of the second mobile phase is subsequently increased to 100% by volume over about 5 minutes. In some aspects, the percentage of the second mobile phase is subsequently maintained at 100% by volume for about 3 minutes. In some aspects, the second mobile phase is subsequently decreased to about 2% by volume over about 2 minutes.

In some aspects, the mass spectrometry is performed using a fragmentor voltage of about 125-350 V. In some aspects, the mass spectrometry is performed using a fragmentor voltage of about 135V. In some aspects, the mass spectrometry is performed using a capillary voltage of about 3-6 kV. In some aspects, the mass spectrometry is performed using a capillary voltage of about 4 kV.

Some aspects of the disclosure are directed to a recombinant AAV (rAAV) comprising a heterogeneous group of capsid proteins that contain a subpopulation with an amino acid modification. In some aspects, the modification is deamidation or oxidation.

In some aspects, the heterogeneous group comprises a deamidated asparagine (N) at one or more of N57, N255, N256, and N263 of AAV. rh74 or the equivalent residues of AAV1, AAV2, AAV3, AAV4, AAVS, AAV6, AAV7, AAV8, AAV9, AAV10, AAV11, AAV12, AAV 13, or AAVrh10, as measured by mass spectrometry and/or ultraviolet (UV)-visible spectroscopy. In another embodiment, the heterogeneous group comprises a deamidated asparagine (N) within a peptide sequence of any one of SEQ ID Nos: 1-5, or its equivalent peptide sequence of other AAV serotype.

In some aspects, the heterogeneous group comprises less than 70%, 60%, 50%, 40%, 30%, 20%, 15%, 10% or 5% of capsid proteins with deamidation at N57 of AAV. rh74 capsid. In some aspects, the heterogeneous group comprises less than 15% of capsid proteins with deamidation at N57 of AAV. rh74 capsid. In some aspects, the heterogeneous group comprises less than 70%, 60%, 50%, 40%, 30%, 20%, 15%, 10%, or 5% of capsid proteins with deamidation at N254 and/or N255 of AAV. rh74 capsid. In some aspects, the heterogeneous group comprises less than 70%, 60%, 50%, 40%, 30%, 20%, 10% or 5% of capsid proteins with deamidation at N263.

In some aspects, the heterogeneous group comprises an oxidized methionine at one or more of M437, M473, M526, M544, M560, and M637 of AAV. Rh74 or the equivalent residues of AAV1, AAV2, AAV3, AAV4, AAVS, AAV6, AAV7, AAV8, AAV9, AAV10, CAAV11, AAV12, AAV 13, or AAVrh10, as measured by mass spectrometry and/or ultraviolet (UV)-visible spectroscopy. In some aspects, the heterogeneous group comprises less than 30%, 20%, 10%, 5%, or 1% of capsid proteins with oxidation at M437. In some aspects, the heterogeneous group comprises less than 30%, 20%, 10%, 5%, or 1% of capsid proteins with oxidation at M473. In some aspects, the heterogeneous group comprises less than 30%, 20%, 10%, 5%, or 3% of capsid proteins with oxidation at M526. In some aspects, the heterogeneous group comprises less than 30%, 20%, 10%, 5%, or 2% of capsid proteins with oxidation at M544. In some aspects, the heterogeneous group comprises less than 30%, 20%, 10%, 5%, or 2% of capsid proteins with oxidation at M560. In some aspects, the heterogeneous group comprises less than 30%, 20%, 10%, 5%, or 1% of capsid proteins with oxidation at M637.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

BRIEF DESCRIPTION OF THE FIGURES

The following figures form part of the present specification and are included to further illustrate aspects of the present invention.

FIG. 5 shows the deamidation results for AAV.rh74 with Tris-HC1 buffer.

FIG. 6 shows the oxidation results for AAV.rh74 with Tris-HC1 buffer.

DETAILED DESCRIPTION

Figure 1:
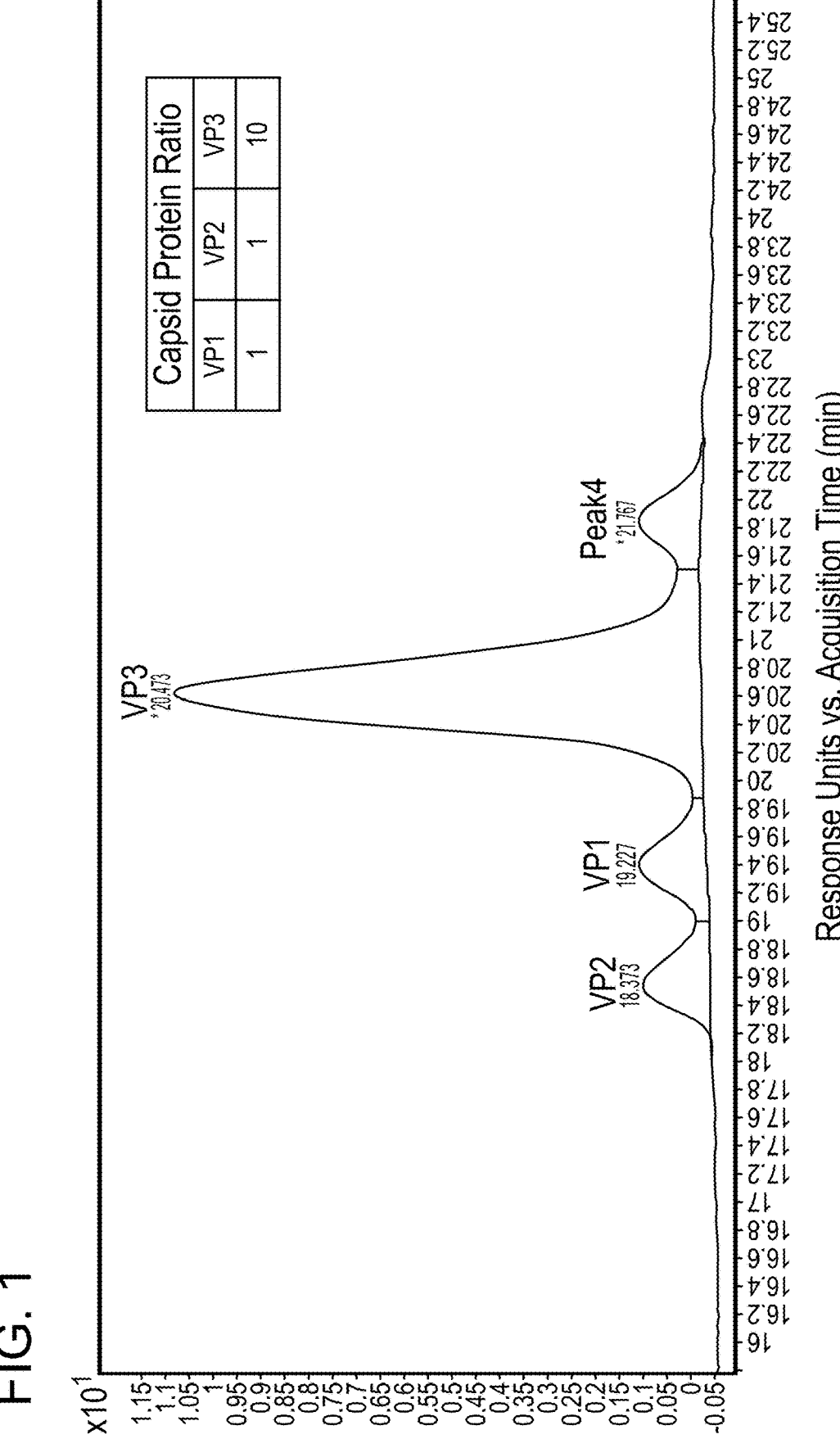
FIG. 1 depicts a UV chromatogram for the AAVrh74 capsid proteins, with integrations confirming the capsid protein ratio.
Figure 2:
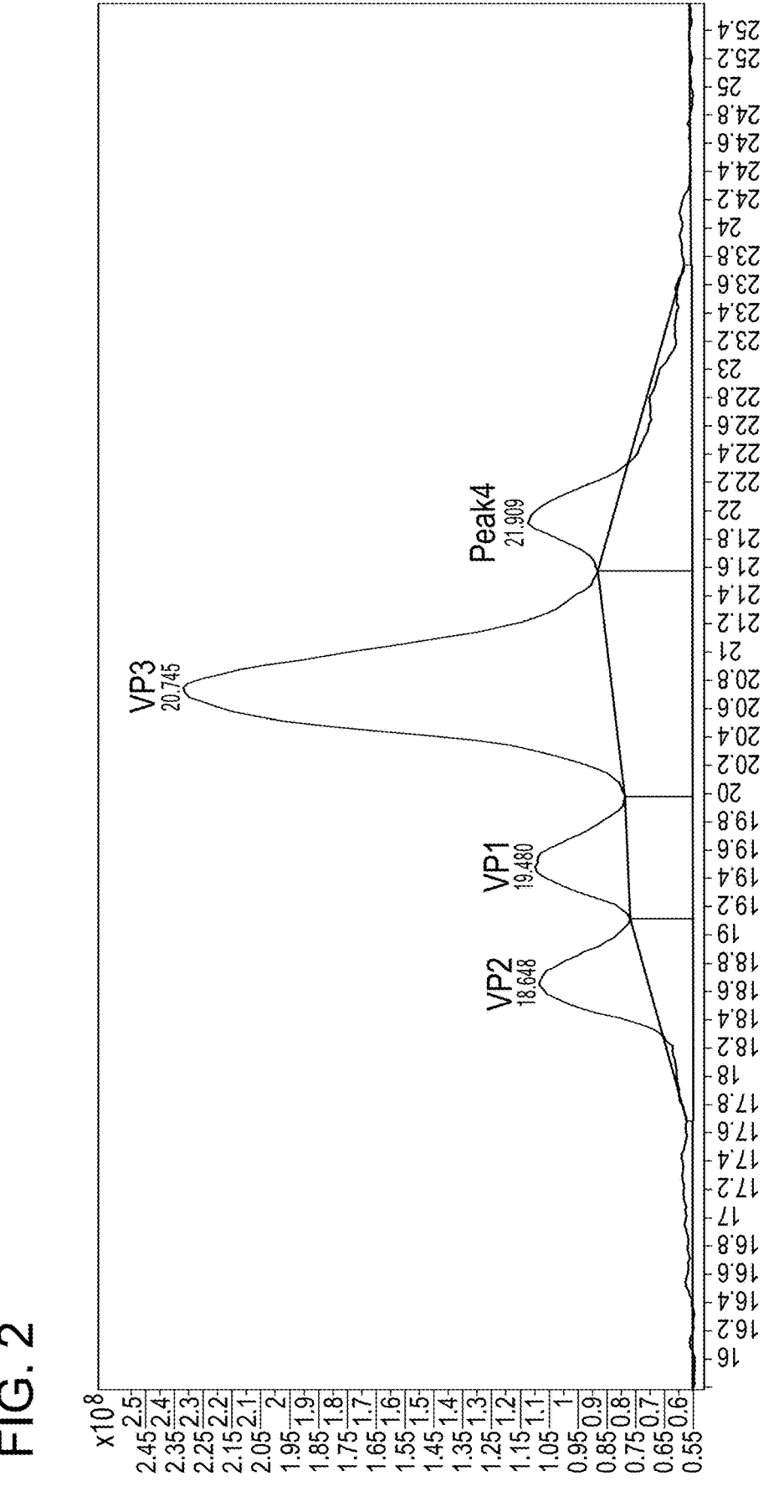
FIG. 2 depicts a total ion chromatogram for the AAVrh74 capsid proteins.
Figure 3A:
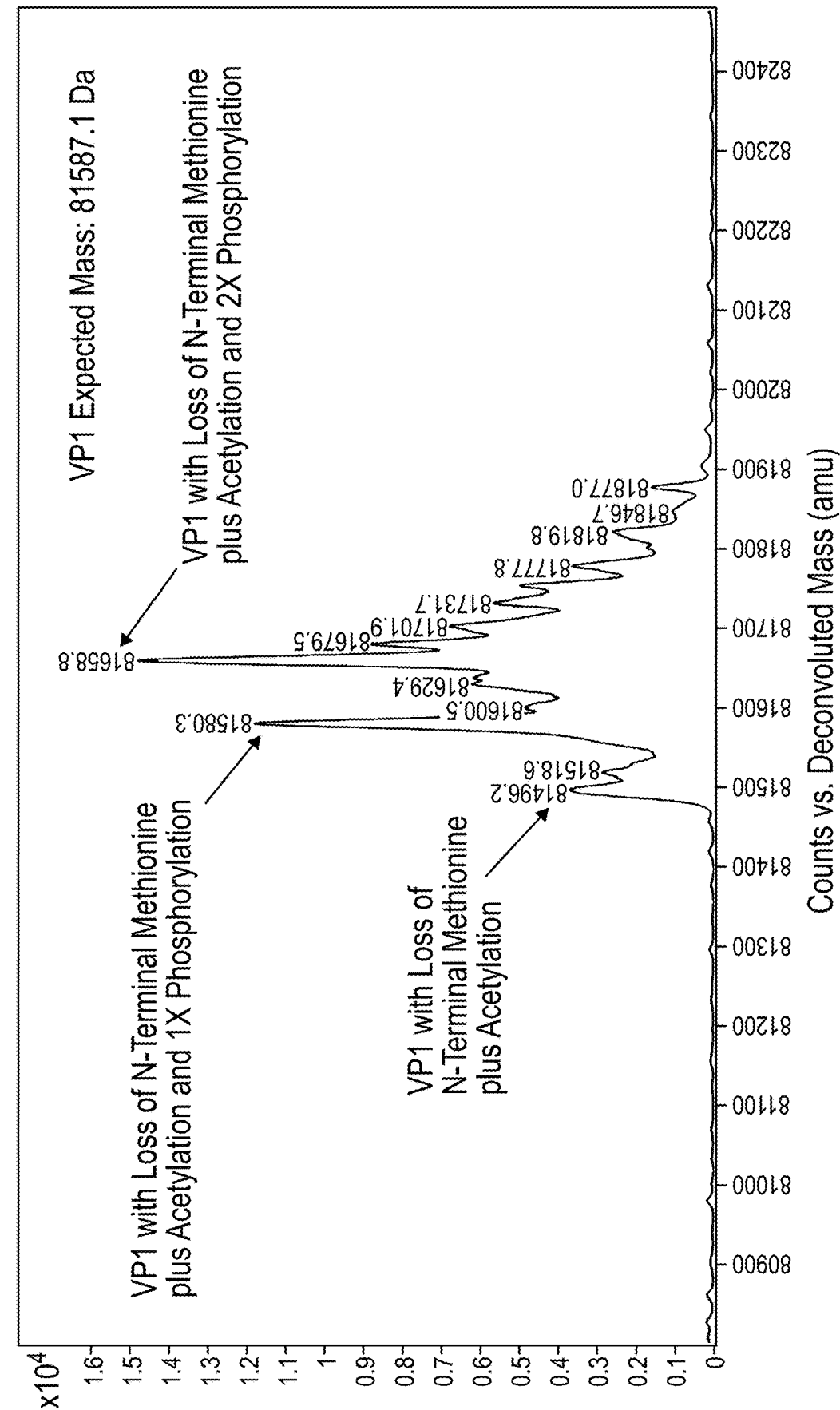
FIG. 3 shows deconvoluted MS spectra for VP1 (FIG. 3A), VP2 (FIG. 3B) and VP3 (FIG. 3C) capsid proteins respectively, confirming the intact masses of all three capsid proteins and detection of post-translation modifications of the capsid proteins.
FIG. 3D shows the deconvoluted MS spectra for VP1 in multiple samples.
FIG. 3E shows the deconvoluted MS spectra for VP2 in multiple samples.
FIG. 3F shows the deconvoluted MS spectra for VP3 in multiple samples.
Figure 3B:
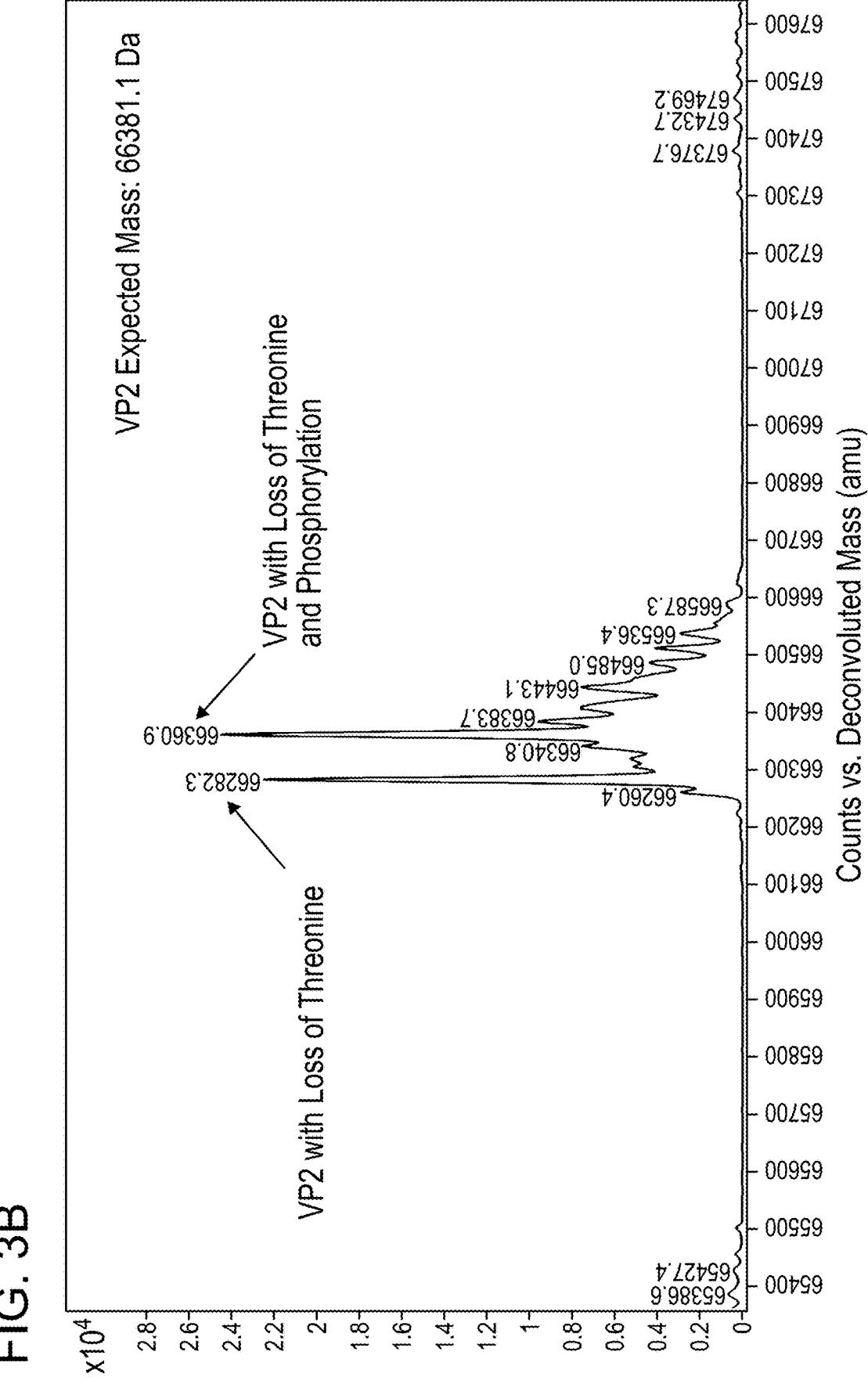
Figure 3C:
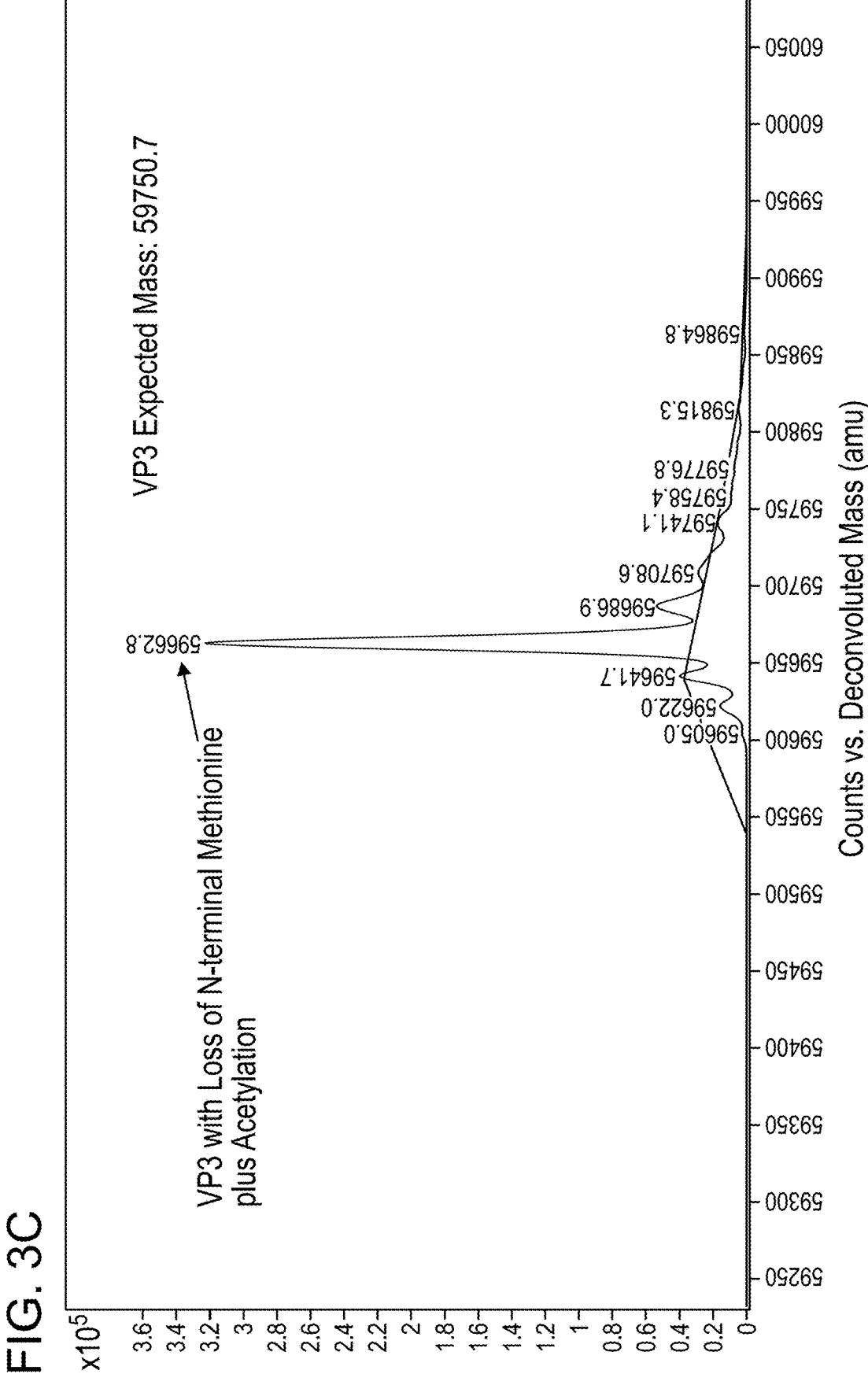
Figure 3D:
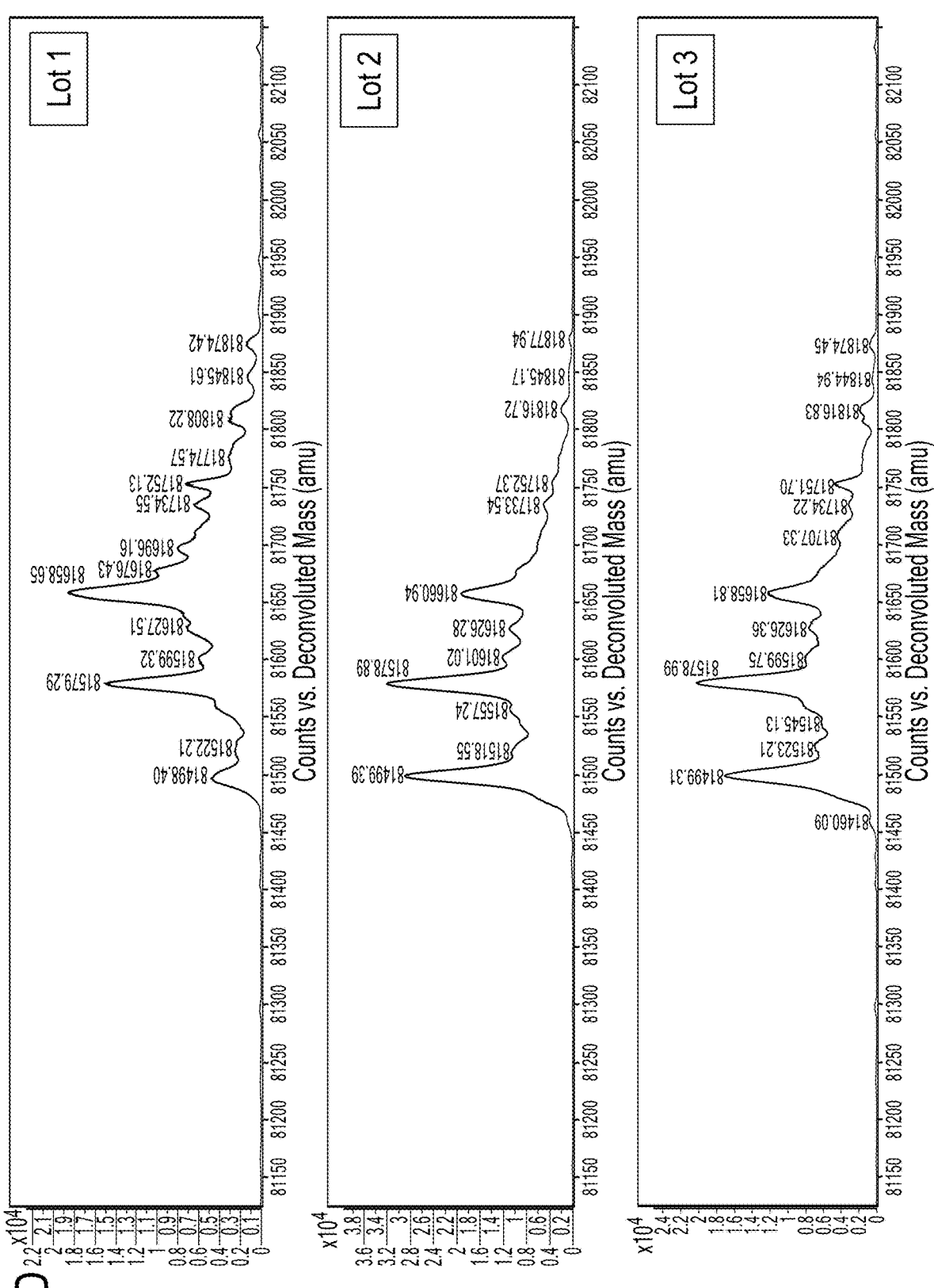
Figure 3E:
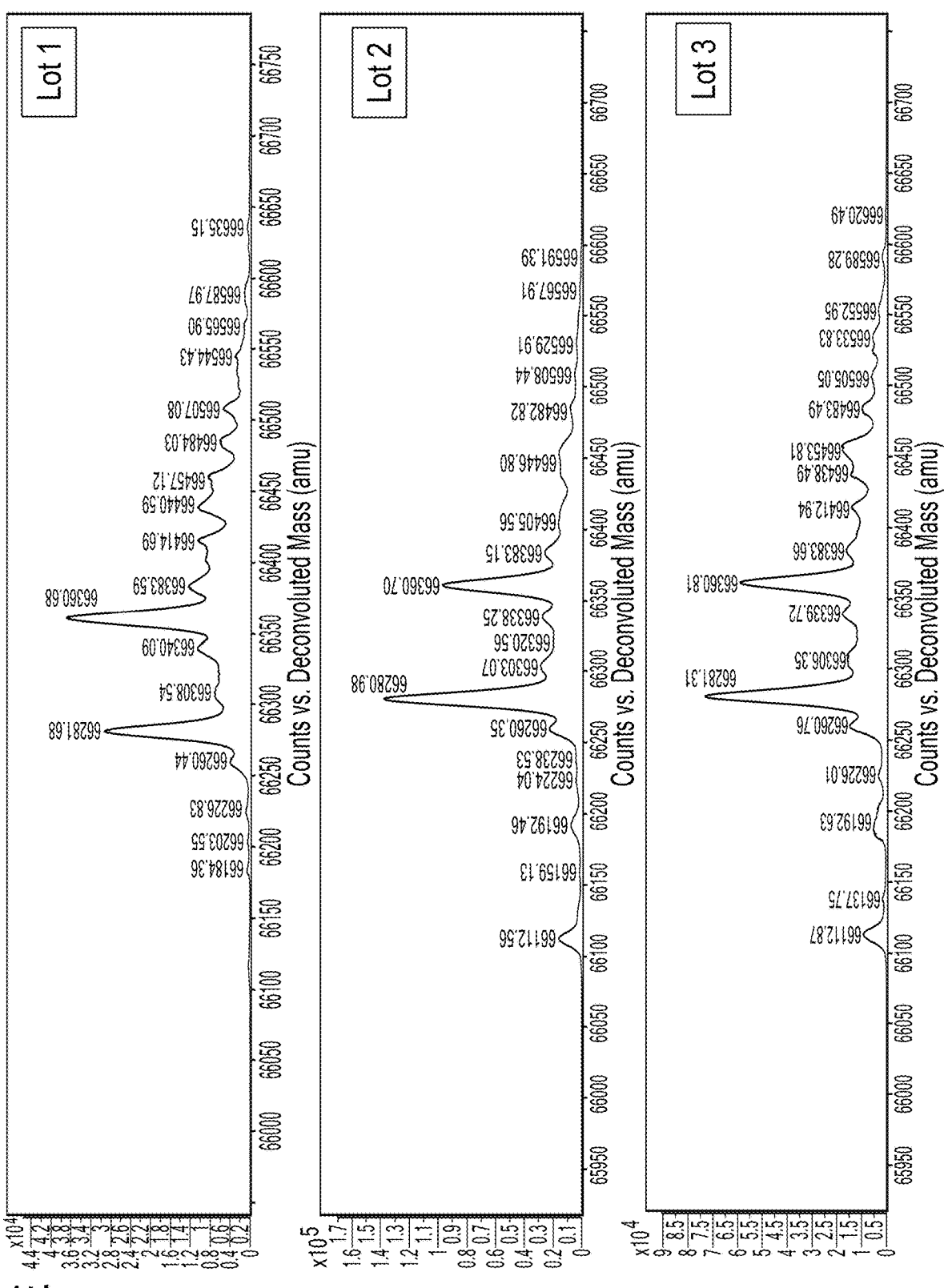
Figure 3F:
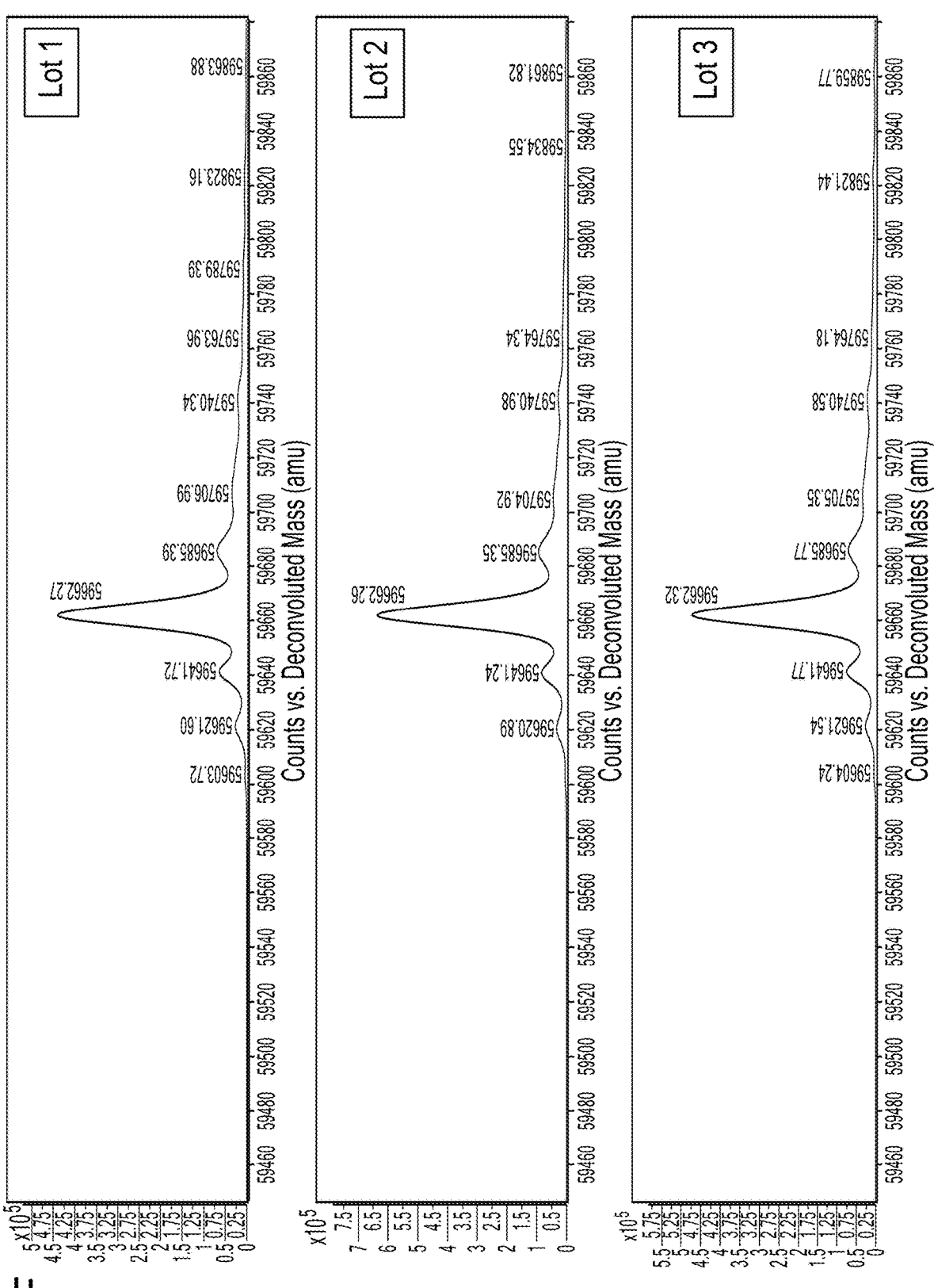

Provided are methods to characterize the VP1, VP2 and VP3 capsid proteins in an adeno-associated virus (AAV) particle using liquid chromatography, mass spectrometry, or ultraviolet (UV)-visible spectroscopy. In some aspects, methods are provided for determining the ratio of VP1, VP2 and VP3 capsid proteins in AAV particle, and/or the masses of one or more of the VP1, VP2 and VP3 capsid proteins. The disclosure also provides methods to characterize the purity of rAAV compositions using liquid chromatography and mass spectrometry.

Definitions

For convenience, before further description of the present invention, certain terms used in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

As used herein, "about" is used to indicate that a value includes the inherent variation of error for the device, the method being employed to determine the value, or the variation that exists among the study subjects. In some aspects, "about" indicates that deviations of 5% to 10% above (e.g., up to 5% to 10% above) and 5% to 10% below (e.g., up to 5% to 10% below) a given value or range remain within the intended meaning of the recited value or range.

The term "AAV" or "adeno-associated virus" refers to a Dependoparvovirus within the Parvoviridae genus of viruses. Herein, AAV can refer to a wild-type virus, or an AAV derived from a naturally occurring wild-type virus, e.g., an AAV derived from a rAAV genome packaged into a capsid derived from capsid proteins encoded by a naturally occurring cap gene and/or a rAAV genome packaged into a capsid derived from capsid proteins encoded by a non-natural capsid cap gene, for example, AAVrh.74.

The AAV can be any serotype, for example AAV1, AAV2, AAV3, AAV4, AAV5, AAV6, AAV7, AAV8, AAV9, AAV-10, AAV-11, AAV-12, AAV-13, AAV rh.10, AAV rh.74, or variants and derivatives thereof In some aspects, the rAAV is of the serotype AAVrh.74. Production of pseudotyped rAAV is disclosed in, for example, WO 01/83692, which is incorporated by reference in its entirety. Other types of rAAV variants, for example rAAV with capsid mutations, are also contemplated. See, for example, Marsic et al., Molecular Therapy, 22(11): 1900-1909 (2014).

As used herein, the term "AAV particle," "AAV vector," "AAV virion," "AAV viral particle," or "AAV vector particle" is used to refer to a viral particle composed of an AAV capsid and an encapsidated AAV genome. The AAV particle, in some aspects, comprises a heterologous polynucleotide (i.e. a polynucleotide other than a wild-type AAV genome such as a transgene to be delivered to a mammalian cell). Production of AAV viral particles, in some aspects, includes production of AAV vector, as such a vector is contained within an AAV vector particle.

For example, a wild-type (wt) AAV virus particle comprising a linear, single-stranded AAV nucleic acid genome associated with an AAV capsid protein coat. The AAV virion can be either a single-stranded (ss) AAV or self-complementary (SC) AAV. In some aspects, a single-stranded AAV nucleic acid molecules of either complementary sense, e.g., "sense" or "antisense" strands, can be packaged into an AAV virion and both strands are equally infectious.

The term "recombinant AAV," or "rAAV" is defined herein as an infectious, replication-defective virus composed of an AAV protein shell, encapsulating a heterologous nucleotide sequence of interest which is flanked on both sides by AAV ITRs. A rAAV, in some aspects, is produced in a suitable host cell which has an AAV vector, AAV helper functions and accessory functions introduced therein. In this manner, the host cell is capable of encoding AAV polypeptides that are required for packaging the AAV vector (containing a recombinant nucleotide sequence of interest) into infectious recombinant virion particles for subsequent gene delivery.

As used herein, the term "capsid protein" refers to a protein that forms the coat or shell of a virus. The term "AAV capsid protein" refers to the protein that forms the coat of an adeno-associated virus (AAV), which is composed of a total of 60 subunits; each subunit is an amino acid sequence, e.g., viral protein 1 (VP1), VP2 or VP3.

As used herein, the term "liquid chromatography (LC)" refers to a technique used to separate, identify, and quantitate components in a mixture. In column liquid chromatography, the liquid mobile phase passes through the column and components of the mobile phase interact with the solid stationary phase. The composition of the mobile phase can be changed during a separation run to alter the strengths of interactions of the compounds of interest. As the mobile phase continues to flow through the column, the eluent is typically collected in fractions while monitoring the concentrations of the compounds eluted from the column over time to produce an elution curve, or chromatogram.

As used herein, the term "stationary phase" refers to the substance that stays fixed in the column. The most commonly used stationary phase columns are carbon chain-bonded silica, phenyl-bonded silica, and cyano-bonded silica. In some aspects, the stationary phase may include a hydrophobic alkyl chain of a particular length, such as C4, C8, or C18. In some aspects, the reverse phase chromatography is a C8 reverse chromatography (e.g., reverse phase chromatography utilizing a C8 stationary phase).

As used herein, the term "mobile phase" refers to water, solvents, or mixtures of water and solvents that are used to elute compounds from columns. The most common mobile phase solvents include but are not limited to acetonitrile, methanol, tertrahydrofuran, ethanol, or isopropyl alcohol. In some aspects, two mobile phases are used. For example, a first mobile phase and a second mobile phase can be mixed in situ to obtain a solvent used for eluting materials from the column. In some aspects, the volume ratio of the second mobile phase to the first mobile phase is in a gradient that increases during the elution step.

As used herein, the term "mass spectrometry" or "MS" refers to an analytical technique that measures the mass-to-charge (m/z) ratio of ions to identify and quantify molecules in simple and complex mixtures. MS technology generally includes: (1) ionizing the compounds to form charged compounds; and (2) detecting the mass-to-charge ratio of the charged compounds and calculating the molecular weight. The compounds may be ionized and detected by any suitable means. A "mass spectrometer" generally includes an ionizer, a mass analyzer, and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). In some mass spectrometry methods, ions may be separated from one another using time-of-flight (TOF), an orbitrap, a Fourier transform ion cyclotron resonance spectrometer, a quadrupole or an ion trap, for example, and then detected using an ion detector.

As used herein, the term "ultraviolet—visible spectroscopy," "ultraviolet—visible spectrophotometry," "UV—Vis," or "UV/Vis" refers to an absorption spectroscopy or a reflectance spectroscopy that is used to determine the optical properties (transmittance, reflectance and absorbance) of liquids and solids. In some aspects, the ultraviolet—visible spectroscopy is used to characterize the capsid proteins of AAV particles.

As used herein, the term "total ion chromatogram (TIC)" refers to a type of chromatogram created by summing up the intensities of all the mass spectral peaks belonging to the same scan.

As used herein, the term "AAVrh74" refers to an AAV particle having AAVrh74 VP1, VP2 and VP3 capsid proteins or variants thereof. An exemplary AAVrh74 VP1 capsid protein sequence is set forth in SEQ ID NO:4 of U.S. Pat. No. 9,909,142, which is hereby incorporated by reference in its entirety. Exemplary variants of AAVrh74 VP1 capsid proteins are also set forth in U.S. Pat. No. 9,909,142.

As used herein, the term "subpopulation" of VP proteins refers to a group of VP proteins which has at least one defined characteristic in common and which consists of at least one group member to less than all members of the reference group, unless otherwise specified. For example, a "subpopulation" of VP1 proteins may be at least one VP1 protein and less than all VP1 proteins in an assembled AAV capsid, unless otherwise specified. A "subpopulation" of VP3 proteins may be one VP3 protein to less than all VP3 proteins in an assembled AAV capsid, unless otherwise specified. For example, VP1 proteins may be a subpopulation of VP proteins; VP2 proteins may be a separate subpopulation of VP proteins, and VP3 are yet a further subpopulation of VP proteins in an assembled AAV capsid. In another example, VP1, VP2 and VP3 proteins may contain subpopulations having different modifications, e.g., at least one, two, three or four highly deamidated asparagines, e.g., at asparagine—glycine pairs.

Characterization of AAV VP1, VP2, and VP3 Capsid Proteins

In some aspects, the present disclosure provides a method to characterize VP1, VP2 and VP3 capsid proteins in an adeno-associated virus (AAV) particle, which comprises subjecting the AAV particle to a liquid chromatography at about 70° C. to about 90° C., wherein the masses and ratio of VP1, VP2 and VP3 capsid proteins are determined by mass spectrometry and/or ultraviolet (UV)-visible spectroscopy. In some aspects, the masses and ratio of VP1, VP2 and VP3 capsid proteins are determined by mass spectrometry and ultraviolet (UV)-visible spectroscopy. In some aspects, the capsids on the AAV particle is denatured into the individual VP1, VP2 and VP3 proteins in the column of the liquid chromatography. In some aspects, the capsid proteins are separated by the liquid chromatography. In some aspects, the method includes (a) subjecting the AAV particle to liquid chromatography to separate the VP1, VP2 and VP3 capsid proteins; and (b) subjecting the separated VP1, VP2 and VP3 capsid proteins produced in step (a) to mass spectrometry and/or ultraviolet-visible spectroscopy to determine the relative amounts of the VP1, VP2 and VP3 capsid proteins, thereby determining the ratio of VP1, VP2 and VP3 capsid proteins in the AAV particle. In some aspects, the liquid chromatography is performed at about 70° C. to about 90° C. In some aspects, the liquid chromatography is performed at about 70° C., 74° C., 76° C., 78° C., 80° C., 82° C., 84° C., 86° C., 88° C., or 90° C. In some aspects, the liquid chromatography is performed at about 80° C.

In some aspects, the method further includes determining the masses of one or more of the VP1, VP2 and VP3 capsid proteins of the AAV particle.

In some aspects, the relative amounts of the VP1, VP2 and VP3 capsid proteins are determined by comparing the total ion chromatogram (TIC) of the VP1, VP2 and VP3 capsid proteins.

In some aspects, the liquid chromatography is reverse phase liquid chromatography, size exclusion chromatography, hydrophilic interaction liquid chromatography, or cation exchange chromatography. In some aspects, the liquid chromatography is reverse phase liquid chromatography.

In some aspects, the reverse phase chromatography is performed using a C18 column, a C8 column, or a C4 column. In some aspects, the liquid chromatography is performed using a C8 column.

In some aspects, the stationary phase of the reverse phase liquid chromatography is comprised within a chromatography column that is about 50-300 mm long and has an internal diameter of about 1-4.6 mm. In some aspects, the column is a BEH column. In some aspects, the column has an internal diameter of 1, 2.1, 3, or 4.6 mm. In some aspects, the column has a length of 50, 75, 100, 150, or 300 mm. In some aspects, the column size is 1 mm×50 mm, 2.1 mm×50 mm, 3 mm×50 mm , 4.6 mm×50 mm, 1 mm×75 mm, 2.1 mm×75 mm, 3 mm×75 mm , 4.6 mm×75 mm, 1 mm×100 mm, 2.1 mm×100 mm, 3 mm×100 mm , 4.6 mm×100 mm, 1 mm×150 mm, 2.1 mm×150 mm, 3 mm×150 mm, 4.6 mm×150 mm, 1 mm×300 mm, 2.1 mm×300 mm, 3 mm×300 mm, or 4.6 mm×300 mm. In some aspects, the column size is 1.6×50 mm, 1.6×60 mm, 1.6×70 mm, 1.6×80 mm, 1.6×90 mm, 1.6×100 mm, 1.6×110 mm, 1.6×120 mm, 1.6×130 mm, 1.6×140 mm, 1.6×150 mm, 1.7×50 mm, 1.7×60, 1.7×70 mm, 1.7×80 mm, 1.7×90 mm, 1.7×100 mm, 1.7×110 mm, 1.7×120 mm, 1.7×130 mm, 1.7×140 mm, 1.7×150 mm, 1.8×50 mm, 1.8×60, 1.8×70 mm, 1.8×80 mm, 1.8×90 mm, 1.8×100 mm, 1.8×110 mm, 1.8×120 mm, 1.8×130 mm, 1.8×140 mm, 1.8×150 mm, 1.9×50 mm, 1.9×60 mm, 1.9×70 mm, 1.9×80 mm, 1.9×90 mm, 1.9×100 mm, 1.9×110 mm, 1.9×120 mm, 1.9×130 mm, 1.9×140 mm, 1.9×150 mm, 2.0×50 mm, 2.0×60 mm, 2.0×70 mm, 2.0×80 mm, 2.0×90 mm, 2.0×100 mm, 2.0×110 mm, 2.0×120 mm, 2.0×130 mm, 2.0×140 mm, 2.0×150 mm, 2.1×50 mm, 2.1×60 mm, 2.1×70 mm, 2.1×80 mm, 2.1×90 mm, 2.1×100 mm, 2.1×110 mm, 2.1×120 mm, 2.1×130 mm, 2.1×140 mm, 2.1×150 mm, 2.2×50 mm, 2.2×60 mm, 2.2×70 mm, 2.2×80 mm, 2.2×90 mm, 2.2×100 mm, 2.2×110 mm, 2.2×120 mm, 2.2×130 mm, 2.2×140 mm, 2.2×150 mm, 2.3×50 mm, 2.3×60 mm, 2.3×70 mm, 2.3×80 mm, 2.3×90 mm, 2.3×100 mm, 2.3×110 mm, 2.3×120 mm, 2.3×130 mm, 2.3×140 mm, 2.3×150 mm, 2.4×50 mm, 2.4×60 mm, 2.4×70 mm, 2.4×80 mm, 2.4×90 mm, 2.4×100 mm, 2.4×110 mm, 2.4×120 mm, 2.4×130 mm, 2.4×140 mm, 2.4×150 mm, 2.5×50 mm, 2.5×60, 2.5×70 mm, 2.5×80 mm, 2.5×90 mm, 2.5×100 mm, 2.5×110 mm, 2.5×120 mm, 2.5×130 mm, 2.5×140 mm, 2.5×150 mm, 2.6×50 mm, 2.6×60 mm, 2.6×70 mm, 2.6×80 mm, 2.6×90 mm, 2.6×100 mm, 2.6×110 mm, 2.6×120 mm, 2.6×130 mm, 2.6×140 mm, or 2.6×150 mm. In some aspects, the stationary phase of the reverse phase liquid chromatography is comprised within a chromatography column that is about 100 mm long and has an internal diameter of about 2.1 mm.

In some aspects, the stationary phase of the reverse phase liquid chromatography comprises particles sized between about 1.2 μm-2.5 μm. In another aspects, the stationary phase of the reverse phase liquid chromatography comprises particles sized at about 1.7 μm, 1.8 μm or 2.1 μm. In some aspects, the particle size is about 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, or 2.5 μm. In some aspects, the stationary phase of the reverse phase liquid chromatography is comprised of particles of about 1.7 μm.

In some aspects, the chromatography uses a first mobile phase including fluoro-substituted acetic acid in water. The fluoro-substituted acetic acids include monofluoroacetic acid, difluoroacetic acid, and trifluoroacetic acid. In some aspects, the chromatography uses a first mobile phase including trifluoroacetic acid in water.

In some aspects, the first mobile phase includes from about 0.05 to about 0.15% of fluoro-substituted acetic acid by volume. In some aspects, the first mobile phase comprises about 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, or 0.2% of fluoro-substituted acetic acid by volume. In some aspects, the first mobile phase comprises about 0.05% or 0.1% of fluoro-substituted acetic acid by volume. In some aspects, the first mobile phase includes about 0.1% of fluoro-substituted acetic acid by volume. In some aspects, the fluoro-substituted acetic acid is trifluoroacetic acid. In some aspects, the first mobile phase includes about 0.1% of trifluoroacetic acid by volume.

In some aspects, the chromatography uses a second mobile phase including fluoro-substituted acetic acid in acetonitrile. In some aspects, the chromatography uses a second mobile phase including trifluoroacetic acid in acetonitrile. In some aspects, the chromatography uses a second mobile phase including fluoro-substituted acetic acid in the mixture of acetonitrile and water. In some aspects, the chromatography uses a second mobile phase including trifluoroacetic acid in the mixture of acetonitrile and water.

In some aspects, the second mobile phase includes about 0.05-0.2% of fluoro-substituted acetic acid by volume. In some aspects, the second mobile phase includes about 0.05-0.15% of fluoro-substituted acetic acid by volume. In some aspects, the second mobile phase includes about 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, or 0.2% of fluoro-substituted acetic acid by volume. In some aspects, the second mobile phase comprises about 0.05% or 0.1% of fluoro-substituted acetic acid by volume. In some aspects, the second mobile phase includes about 0.1% fluoro-substituted acetic acid. In some aspects, the fluoro-substituted acetic acid is trifluoroacetic acid. In some aspects, the second mobile phase includes about 0.1% trifluoroacetic acid.

In some aspects, the second mobile phase includes about 75-95% of acetonitrile by volume. In some aspects, the second mobile phase includes about 75%, 80%, 85%, 90%, or 95% of acetonitrile by volume. In some aspects, the second mobile phase includes about 90% acetonitrile and 10% water by volume.

In some aspects, the percentage of the second mobile phase, in the combination of the first mobile phase and the second mobile phase, in the chromatography is increased over time. In some aspects, the percentage of the second mobile phase is increased from about 10% to about 40% by volume. In some aspects, the percentage of the second mobile phase is increased from about 10% to about 45% by volume. In some aspects, the percentage of the second mobile phase is increased from about 10% to about 100% by volume. In some aspects, the percentage of the second mobile phase is increased from about 10% to about 45% in about 30-40 minutes. In some aspects, the percentage of the second mobile phase is increased from about 10% to about 45% in about 35 minutes. In some aspects, the percentage of the second mobile phase is increased from about 10% to about 100% by volume in about 30-50 minutes. In some aspects, the percentage of the second mobile phase is increased from about 10% to about 100% by volume in about 36 minutes.

In some aspects, the percentage of the second mobile phase is increased from about 10% to about 40% by volume in about 5-10 minutes, from about 40% to about 45% in about 25-35 minutes. In some aspects, the percentage of the second mobile phase is increased from about 45% to about 100% in about 0.5-2 minutes. In some aspects, the percentage of the second mobile phase is decreased from about 100% to about 10% in about 0.5-2 minutes.

In some aspects, the percentage of the second mobile phase is increased from about 10% to about 40% by volume in about 6 minutes, from about 40% to about 45% in about 29 minutes. In some aspects, the percentage of the second mobile phase is increased from about 45% to about 100% in about 1 minute. In some aspects, the percentage of the second mobile phase is decreased from about 100% to about 10% in about 1 minute.

In some aspects, the liquid chromatography is high-pressure liquid chromatography (HPLC). In some aspects, the liquid chromatography is ultra-high pressure liquid chromatography (UHPLC).

In some aspects, the mass spectrometry may use any ionization modes, particularly those modes suitable for analyzing biological molecules including, but not limited to, direct infusion-mass spectrometry, electrospray ionization (ESI)-MS, desorption electrospray ionization (DESI)-MS, direct analysis in real-time (DART)-MS, atmospheric pressure chemical ionization (APCI)-MS, electron impact (EI) or chemical ionization (CI), matrix-assisted laser desorption/ionization (MALDI)-MS, and Atmospheric Pressure Ionization-Electrospray (API-ES). In some aspects, the mass spectrometry uses API-ES ionization mode.

In some aspects, the mass spectrometry scans signals over a range of 400-16000 m/z. In some aspects, the mass spectrometry scans signals over a range of 700-13700 m/z.

In some aspects, the scan type of the mass spectrometry is positive polarity. In some aspects, the data acquisition time of the mass spectrometry is about 10-35 minutes. In some aspects, the data acquisition time of the mass spectrometry is about 17-28 minutes.

In some aspects, the nozzle voltage of the mass spectrometry is about 400-600 V. In some aspects, the nozzle voltage of the mass spectrometry is about 500 V. In some aspects, the skimmer voltage of the mass spectrometry is about 60-70 V. In some aspects, the skimmer voltage of the mass spectrometry is about 65 V. In some aspects, the difference between the nozzle and skimmer voltage is about 400-450 V. In some aspects, the difference between the nozzle and skimmer voltage is about 435 V.

In some aspects, the drying gas temperature of the mass spectrometry is about 200-350° C. In some aspects, the drying gas temperature of the mass spectrometry is about 300° C. In some aspects, the drying gas flow rate of the mass spectrometry is about 5-13 L/min. In some aspects, the drying gas flow rate of the mass spectrometry is about 13 L/min.

In some aspects, the mass spectrometry uses a capillary voltage of about 3-6 kV. In some aspects, the mass spectrometry uses a capillary voltage of about 3, 4, 5, or 6 kV. In some aspects, the mass spectrometry uses a capillary voltage of about 5 kV.

In some aspects, the mass spectrometry uses a fragmentor voltage of about 125-350 V. In some aspects, the mass spectrometry uses a fragmentor voltage of about 125, 130, 135, 145, 155, 160, 165, 175, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, or 350V. In some aspects, the mass spectrometry uses a fragmentor voltage of about 175 V.

In some aspects, the AAV particle is AAV1, AAV2, AAV3, AAV4, AAV5, AAV6, AAV7, AAV8, AAV9, AAV10, AAV11, AAV12, AAV13, AAVrh10, AAVrh74 or any naturally occurring, recombinant, or synthetic AAV particles. In some aspects, the AAV particle is a recombinant AAV (rAAV) particle. In some aspects, the AAV particle is AAVrh74.

In some above aspects, the disclosure further includes determining post translational modification of at least one of VP1, VP2 and VP3 capsid proteins. In some aspects, the disclosure further includes determining post translational glycosylation, sialylation, acetylation, loss of amino acid, amidation, phosphorylation, formylation, hydroxylation, methylation, and/or sulfation of at least one of VP1, VP2 and VP3 capsid proteins. The post translational modification comprises one or more of loss of N-terminal methionine, loss of threonine, phosphorylation, and acetylation.

In some aspects, the disclosure includes determining removal of N-terminal methionine in VP1, VP2, or VP3 capsid proteins. In some aspects, the disclosure includes determining removal of N-terminal methionine in VP1 or VP3 capsid proteins. In some aspects, the disclosure includes determining N-terminal acetylation after removal of N-terminal methionine in VP1, VP2, or VP3 capsid proteins. In some aspects, the disclosure includes determining N-terminal acetylation after removal of N-terminal methionine in VP1 or VP3 capsid proteins.

In some aspects, the disclosure provides a method to characterize capsid proteins of an AAV particle at least based in part on the ratio of VP1, VP2 and VP3 capsid proteins and/or the masses of one or more of the VP1, VP2 and VP3 capsid proteins in an AAV particle.

In some aspects, the disclosure provides a method to determine the serotype of an AAV particle at least based in part on the ratio of VP1, VP2 and VP3 capsid proteins in an AAV particle and/or the masses of one or more of the VP1, VP2 and VP3 capsid proteins, wherein the ratio of VP1, VP2 and VP3 capsid proteins and the masses of one or more of the VP1, VP2 and VP3 capsid proteins are determined by the methods disclosed herein.

Mass Spectrometry is an analytical technique for protein characterization. In some aspects, a method for the characterization of the AAVrh74 capsid protein ratio along with the intact mass for all three capsid proteins by liquid chromatography and mass spectrometry is provided. In some aspects, the AAVrh74 capsid is denatured on-column into the individual capsid proteins VP1, VP2, and VP3. The denaturation is achieved by heating the column compartment to 80° C. (3,4). The capsid proteins are then baseline resolved on a Waters BEH C8 column with the help of trifluoroacetic acid, as an ion-pairing agent in the mobile phases (5). The denatured proteins are first analyzed in the UV to achieve the capsid ratio and then in the mass spectrometer to obtain the intact mass for the individual proteins.

Deamidation is a common Post-Translational Modification resulting in the conversion of an asparagine residue to a mixture of isoaspartate and aspartate. Deamidation of glutamine residues also occurs, but at a much slower rate. Oxidation is also a common Post-Translational Modification which a result of the reaction of proteins with a variety of free radicals and reactive oxygen species. Methionine Oxidation is most common, however oxidation of several other amino acid residues like cysteine and tryptophan have also been observed. Deamidation/Oxidation are also common degradation pathways for proteins occurring during manufacturing and storage. Deamidation can have an impact on the activity and stability of proteins. Oxidation can cause conformational changes in proteins and therefore impact protein activity and stability. Oxidation can also impact the immunogenicity of proteins. Therefore, Critical Quality Attributes (CQAs) for proteins needs to be monitored carefully on the post-translation modifications.

The current method with ammonium bicarbonate generated false signals or overestimated the deamidation in AAV capsid protein (Table 7). Here, the disclosure provides a method to more accurate measure post-translation modification on the capsid proteins with Tris-HCl. In some aspects, the LC MS method uses a buffer comprising Tris-HCl. In some aspects, the buffer comprises acetonitrile. In some aspects, the buffer comprises methionine. In some aspects, the buffer comprises Tris-HCl at 5mM to 50 mM, 5%-20% acetonitrile, and methionine at 1 mM to 50 mM. In some aspects, the buffer comprises Tris-HCl at 20 mM, 5%-10% acetonitrile, and methionine at 10 mM.

In some aspects, the post-translation modification comprises deamidation at one or more of N263, N514, N57, N502, N254, and N94 of AAV8 or its equivalent residue at AAV1, AAV2, AAV3, AAV4, AAV5, AAV6, AAV7, AAV9, AAV10, AAV11, AAV12, AAV 13, AAVrh10, or AAVrh74. In some aspects, the post-translation modification comprises deamidation at one or more of N57, N255, N256, and N263 of AAV. Rh74. In some aspects, the post-translation modification comprises oxidation at one or more of M437, M473, M526, M544, M560, and M637 of AAV. Rh74.

AAV Compositions

Some aspects of the disclosure are directed to a recombinant AAV (rAAV) comprising a heterogeneous group of capsid proteins that contain a subpopulation with an amino acid modification. In some aspects, the modification can be deamidation, acetylation, isomerization, phosphorylation, or oxidation. In some aspects, the modification is deamidation or oxidation.

In some aspects, the rAAV capsid can contain subpopulations of VP1, VP2 and VP3 having at least 1, at least 2, at least 3, at least 4, at least 5 to at least about 25 deamidated amino acid residues, of which at least about 1% to about 10%, at least about 10% to about 25%, at least about 25% to about 50%, at least about 50% to about 70%, at least about 70% to about 100%, at least about 75% to about 100%, at least about 80% to about 100% or at least about 90% to about 100% are deamidated as compared to the encoded amino acid sequence of the VP proteins. In some aspects, the majority of these can be N residues. In some aspects, Q residues can be deamidated.

In some aspects, the disclosure provides an AAV composition comprising an AAV capsid that comprises deamidation at one or more of N57, N255, N256, and N263 of AAV. Rh74, or the equivalent residues of AAV1, AAV2, AAV3, AAV4, AAV5, AAV6, AAV7, AAV8, AAV9, AAV10, AAV11, AAV12, AAV 13, or AAVrh10 as measured by mass spectrometry and/or ultraviolet (UV)-visible spectroscopy. In some aspects, the deamidation is measured by any of the methods disclosed herein.

In some aspects, the heterogeneous group comprises less than about 80%, less than about 78%, less than about 76%, less than about 74%, less than about 72%, less than about 70%, less than about 68%, less than about 66%, less than about 64%, less than about 62%, less than about 60%, less than about 58%, less than about 56%, less than about 54%, less than about 52%, less than about 50%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 15%, less than about 14%, less than about 13%, less than about 12%, less than about 11%, or less than about 10% of capsid proteins with deamidation at N57 of AAV. rh74 capsid.

In some aspects, wherein the heterogeneous group comprises less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, or less than about 10% of capsid proteins with deamidation at N57 of AAV. rh74 capsid.

In some aspects, the heterogeneous group comprises less than about 80%, less than about 78%, less than about 76%, less than about 74%, less than about 72%, less than about 70%, less than about 68%, less than about 66%, less than about 64%, less than about 62%, less than about 60%, less than about 58%, less than about 56%, less than about 54%, less than about 52%, less than about 50%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 15%, less than about 14%, less than about 13%, less than about 12%, less than about 11%, or less than about 10%, less than about 8%, less than about 7%, less than about 6%, less than about 5%, less than about 4%, less than about 3%, less than about 2%, or less than about 1% of capsid proteins with deamidation at N254 and/or N255 of AAV. rh74 capsid.

In some aspects, the heterogeneous group comprises less than about 80%, less than about 78%, less than about 76%, less than about 74%, less than about 72%, less than about 70%, less than about 68%, less than about 66%, less than about 64%, less than about 62%, less than about 60%, less than about 58%, less than about 56%, less than about 54%, less than about 52%, less than about 50%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 15%, less than about 14%, less than about 13%, less than about 12%, less than about 11%, or less than about 10% of capsid proteins with deamidation at N263.

In some aspects, the AAV composition comprises an AAV capsid that comprises oxidation at one or more of M437, M473, M526, M544, M560, and M637 of AAV. Rh74 or the equivalent residues of AAV1, AAV2, AAV3, AAV4, AAV5, AAV6, AAV7, AAV8, AAV9, AAV10, AAV11, AAV12, AAV 13, or AAVrh10 as measured by mass spectrometry and/or ultraviolet (UV)-visible spectroscopy. In some aspects, the deamidation is measured by any of the methods disclosed herein.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M437.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M473.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M526.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M544.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M560.

In some aspects, the heterogeneous group comprises less than about 40%, less than about 48%, less than about 46%, less than about 44%, less than about 42%, less than about 40%, less than about 38%, less than about 36%, less than about 34%, less than about 32%, less than about 30%, less than about 28%, less than about 26%, less than about 24%, less than about 22%, less than about 20%, less than about 18%, less than about 16%, less than about 14%, less than about 12%, less than about 10%, less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, or less than 0.5% of capsid proteins with oxidation at M637.

Characterization of Host Cell Proteins in an AAV Composition

In some aspects, the disclosure provides a method of characterizing host cell proteins in an AAV composition, such as an AAV based gene therapy drug product. In some aspects, the method of characterizing host cell protein sin an AAV composition comprises immunoprecipitating viral capsid proteins from the compositions, digesting residual host cell proteins, and analyzing the digested proteins with liquid chromatography quadrupole time of flight mass spectrometry (LC-QTOF-MS) to identify host cell proteins. As used herein, the term "residual host cell proteins" or "residual proteins" means the protein remaining in solution after immunoprecipitation. In some aspects, the method further comprises analyzing the digested host cell proteins with iterative MS/MS.

In some aspects, immunoprecipitation comprises incubating the AAV composition with an VP antibody. In some aspects, the VP antibody comprises an anti-AAV VP1 antibody, an anti-AAV VP2 antibody, an anti-AAV VP3 antibody, or combinations thereof. In some aspects, the antibody can be anti-Adeno-associated virus (AAV), VP1/VP2/VP3 from American Research Products, Inc. (Catalog #:03-61058)

In some aspects, the residual host cell proteins are digested in solution. In some aspects, the digestion is rapid digestion. In some aspects, rapid digestion is performed at about 60° C. to about 80° C. In some aspects, rapid digestion is performed at about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., or about 80° C. In some aspects, the rapid digestion is performed at about 70° C.

In some aspects, the AAV composition is spiked with a known amount of at least one known protein standard. In some aspects, the at least one known protein standard is a human or bovine protein standard. In some aspects, the method further comprises quantifying the amount of the residual host cell proteins relative to the at least one known protein standard.

In some aspects, the liquid chromatography is reverse phase liquid chromatography, size exclusion chromatography, hydrophilic interaction liquid chromatography, or cation exchange chromatography. In some aspects, the liquid chromatography is reverse phase liquid chromatography.

In some aspects, the liquid chromatography is performed at about 35° C. to about 55° C. In some aspects, the liquid chromatography is performed at about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., or about 55° C. In some aspects, the liquid chromatography is performed at about 45° C.

In some aspects, the reverse phase chromatography is performed using a C18 column, a C8 column, or a C4 column. In some aspects, the liquid chromatography is performed using a C8 column.

In some aspects, the stationary phase of the reverse phase liquid chromatography is comprised within a chromatography column that is about 50-300 mm long and has an internal diameter of about 1-4.6 mm. In some aspects, the column is a BEH column. In some aspects, the column has an internal diameter of 1, 2.1, 3, or 4.6 mm. In some aspects, the column has a length of 50, 75, 100, 150, or 300 mm. In some aspects, the column size is 1 mm×50 mm, 2.1 mm×50 mm, 3 mm×50 mm , 4.6 mm×50 mm, 1 mm×75 mm, 2.1 mm×75 mm, 3 mm×75 mm , 4.6 mm×75 mm, 1 mm×100 mm, 2.1 mm×100 mm, 3 mm×100 mm , 4.6 mm×100 mm, 1 mm×150 mm, 2.1 mm×150 mm, 3 mm×150 mm, 4.6 mm×150 mm, 1 mm×300 mm, 2.1 mm×300 mm, 3 mm×300 mm, or 4.6 mm×300 mm. In some aspects, the column size is 1.6×50 mm, 1.6×60 mm, 1.6×70 mm, 1.6×80 mm, 1.6×90 mm, 1.6×100 mm, 1.6×110 mm, 1.6×120 mm, 1.6×130 mm, 1.6×140 mm, 1.6×150 mm, 1.7×50 mm, 1.7×60, 1.7×70 mm, 1.7×80 mm, 1.7×90 mm, 1.7×100 mm, 1.7×110 mm, 1.7×120 mm, 1.7×130 mm, 1.7×140 mm, 1.7×150 mm, 1.8×50 mm, 1.8×60, 1.8×70 mm, 1.8×80 mm, 1.8×90 mm, 1.8×100 mm, 1.8×110 mm, 1.8×120 mm, 1.8×130 mm, 1.8×140 mm, 1.8×150 mm, 1.9×50 mm, 1.9×60 mm, 1.9×70 mm, 1.9×80 mm, 1.9×90 mm, 1.9×100 mm, 1.9×110 mm, 1.9×120 mm, 1.9×130 mm, 1.9×140 mm, 1.9×150 mm, 2.0×50 mm, 2.0×60 mm, 2.0×70 mm, 2.0×80 mm, 2.0×90 mm, 2.0×100 mm, 2.0×110 mm, 2.0×120 mm, 2.0×130 mm, 2.0×140 mm, 2.0×150 mm, 2.1×50 mm, 2.1×60 mm, 2.1×70 mm, 2.1×80 mm, 2.1×90 mm, 2.1×100 mm, 2.1×110 mm, 2.1×120 mm, 2.1×130 mm, 2.1×140 mm, 2.1×150 mm, 2.2×50 mm, 2.2×60 mm, 2.2×70 mm, 2.2×80 mm, 2.2×90 mm, 2.2×100 mm, 2.2×110 mm, 2.2×120 mm, 2.2×130 mm, 2.2×140 mm, 2.2×150 mm, 2.3×50 mm, 2.3×60 mm, 2.3×70 mm, 2.3×80 mm, 2.3×90 mm, 2.3×100 mm, 2.3×110 mm, 2.3×120 mm, 2.3×130 mm, 2.3×140 mm, 2.3×150 mm, 2.4×50 mm, 2.4×60 mm, 2.4×70 mm, 2.4×80 mm, 2.4×90 mm, 2.4×100 mm, 2.4×110 mm, 2.4×120 mm, 2.4×130 mm, 2.4×140 mm, 2.4×150 mm, 2.5×50 mm, 2.5×60, 2.5×70 mm, 2.5×80 mm, 2.5×90 mm, 2.5×100 mm, 2.5×110 mm, 2.5×120 mm, 2.5×130 mm, 2.5×140 mm, 2.5×150 mm, 2.6×50 mm, 2.6×60 mm, 2.6×70 mm, 2.6×80 mm, 2.6×90 mm, 2.6×100 mm, 2.6×110 mm, 2.6×120 mm, 2.6×130 mm, 2.6×140 mm, or 2.6×150 mm. In some aspects, the stationary phase of the reverse phase liquid chromatography is comprised within a chromatography column that is about 150 mm long and has an internal diameter of about 2.1 mm.

In some aspects, the stationary phase of the reverse phase liquid chromatography comprises particles sized between about 1.2 μm-2.5 μm. In some aspects, the stationary phase of the reverse phase liquid chromatography comprises particles sized at about 1.7 μm, 1.8 μm or 2.1 μm. In some aspects, the particle size is about 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, or 2.5 μm. In some aspects, the stationary phase of the reverse phase liquid chromatography is comprised of particles of about 1.7 μm.

In some aspects, the chromatography uses a first mobile phase including fluoro-substituted acetic acid in water. The fluoro-substituted acetic acids include monofluoroacetic acid, difluoroacetic acid, and trifluoroacetic acid. In some aspects, the chromatography uses a first mobile phase including trifluoroacetic acid in water.

In some aspects, the chromatography uses a first mobile phase including formic acid.

In some aspects, the first mobile phase includes from about 0.05 to about 0.15% of formic acid by volume. In some aspects, the first mobile phase comprises about 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, or 0.2% of formic acid by volume. In some aspects, the first mobile phase comprises about 0.05% or 0.1% of formic acid by volume. In some aspects, the first mobile phase includes about 0.1% of formic acid by volume.

In some aspects, the chromatography uses a second mobile phase including fluoro-substituted acetic acid in acetonitrile. In some aspects, the chromatography uses a second mobile phase including trifluoroacetic acid in acetonitrile. In some aspects, the chromatography uses a second mobile phase including fluoro-substituted acetic acid in the mixture of acetonitrile and water. In some aspects, the chromatography uses a second mobile phase including trifluoroacetic acid in the mixture of acetonitrile and water.

In some aspects, the chromatography uses a second mobile phase including formic acid in acetonitrile. In some aspects, the chromatography uses a second mobile phase including formic acid in the mixture of acetonitrile and water.

In some aspects, the second mobile phase includes about 0.05-0.2% of formic acid by volume. In some aspects, the second mobile phase includes about 0.05-0.15% of formic acid by volume. In some aspects, the second mobile phase includes about 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, or 0.2% of formic acid by volume. In some aspects, the second mobile phase comprises about 0.05% or 0.1% of formic acid by volume. In some aspects, the second mobile phase includes about 0.1% formic acid by volume.

In some aspects, the second mobile phase includes about 75-95% of acetonitrile by volume. In some aspects, the second mobile phase includes about 75%, 80%, 85%, 90%, or 95% of acetonitrile by volume. In some aspects, the second mobile phase includes about 90% acetonitrile and about 10% water by volume.

In some aspects, the percentage of the second mobile phase, in the combination of the first mobile phase and the second mobile phase, in the chromatography is increased over time. In some aspects, the percentage of the second mobile phase is increased from about 2% to about 50% by volume. In some aspects, the percentage of the second mobile phase is increased from about 50% to about 100% by volume. In some aspects, the percentage of the second mobile phase is increased from about 2% to about 50% in about 110-130 minutes. In some aspects, the percentage of the second mobile phase is increased from about 2% to about 50% in about 120 minutes. In some aspects, the percentage of the second mobile phase is increased from about 50% to about 100% by volume in about 20-30 minutes. In some aspects, the percentage of the second mobile phase is increased from about 50% to about 100% by volume in about 25 minutes. In some aspects, the percentage of the second mobile phase is subsequently increased to 100% by volume over about 5 minutes. In some aspects, the percentage of the second mobile phase is subsequently maintained at 100% by volume for about 3 minutes. In some aspects, the second mobile phase is subsequently decreased to about 2% by volume over about 2 minutes.

In some aspects, the percentage of the second mobile phase is maintained at about 100% by volume for about 0.5-1.5 minutes. In some aspects, the percentage of the second mobile phase is maintained at 100% by volume for about 1 minute.

In some aspects, the percentage of the second mobile phase is decreased from about 100% to about 2% in about 1-10 minutes. In some aspects, the percentage of the second mobile phase is decreased from about 100% to about 2% in about 4 minutes.

In some aspects, the liquid chromatography is high-pressure liquid chromatography (HPLC). In some aspects, the liquid chromatography is ultra-high pressure liquid chromatography (UHPLC).

In some aspects, the mass spectrometry may use any ionization modes, particularly those modes suitable for analyzing biological molecules including, but not limited to, direct infusion-mass spectrometry, electrospray ionization (ESI)-MS, desorption electrospray ionization (DESI)-MS, direct analysis in real-time (DART)-MS, atmospheric pressure chemical ionization (APCI)-MS, electron impact (EI) or chemical ionization (CI), matrix-assisted laser desorption/ionization (MALDI)-MS, and Atmospheric Pressure Ionization-Electrospray (API-ES). In some aspects, the mass spectrometry uses API-ES ionization mode.

In some aspects, the mass spectrometry scans signals over a range of 40-5000 m/z. In some aspects, the mass spectrometry scans signals over a range of 50-3000 m/z. In some aspects, the mass spectrometry scans signals over a range of 300-3000 m/z.

In some aspects, the scan type of the mass spectrometry is positive polarity. In some aspects, the data acquisition time of the mass spectrometry is about 1-130 minutes. In some aspects, the data acquisition time of the mass spectrometry is about 2-120 minutes.

In some aspects, the nozzle voltage of the mass spectrometry is about 400-600 V. In some aspects, the nozzle voltage of the mass spectrometry is about 500 V. In some aspects, the skimmer voltage of the mass spectrometry is about 60-70 V. In some aspects, the skimmer voltage of the mass spectrometry is about 65 V. In some aspects, the difference between the nozzle and skimmer voltage is about 400-450 V. In some aspects, the difference between the nozzle and skimmer voltage is about 435 V.

In some aspects, the drying gas temperature of the mass spectrometry is about 200-375° C. In some aspects, the drying gas temperature of the mass spectrometry is about 325° C. In some aspects, the drying gas flow rate of the mass spectrometry is about 5-13 L/min. In some aspects, the drying gas flow rate of the mass spectrometry is about 12 L/min.

In some aspects, the mass spectrometry uses a capillary voltage of about 3-6 kV. In some aspects, the mass spectrometry uses a capillary voltage of about 3, 4, 5, or 6 kV. In some aspects, the mass spectrometry uses a capillary voltage of about 5 kV.

In some aspects, the mass spectrometry uses a fragmentor voltage of about 125-350 V. In some aspects, the mass spectrometry uses a fragmentor voltage of about 125, 130, 135, 145, 155, 160, 165, 175, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, or 350V. In some aspects, the mass spectrometry uses a fragmentor voltage of about 135 V.

Although the subject matter has been described in considerable detail with reference to certain aspects thereof, other aspects are possible. As such, the spirit and scope of the appended claims should not be limited to the description of the specific aspects contained therein.

EXAMPLE

The disclosure will now be illustrated with working examples, and which is intended to illustrate the working of disclosure and not intended to restrict any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

General Methods and Equipment 1.1 Reagents

LCMS water, acetonitrile, and trifluoroacetic acid were obtained from Fisher Scientific and ammonium bicarbonate was obtained from Sigma Aldrich. Table 1 provides reagents used in liquid chromatography and solution preparation.

TABLE 1

| Reagents used for liquid chromatography | | | |
| --- | --- | --- | --- |
| Reagent Name | CAS Number | Required Grade, Purity or Concentration | Suggested Source/ Catalog Number |
| LCMS Water | 7732-18-5 | LCMS | Fisher/W6 |
| Acetonitrile | 67-63-0 | LCMS | Fisher/A955 |
| Trifluoroacetic Acid | 76-05-1 | LCMS | Fisher/A11610X1AMP |
| Ammonium Bicarbonate | 1066-33-7 | BioUltra | Sigma Aldrich/09830 |

1.2 Equipment

The following equipment was used to perform the examples disclosed herein.

a) Waters ACQUITY UPLC BEH C8 Column, 2.1×100 mm, 1.7 μm; Part no. 186002878 b) Pierce Detergent Removal Spin Columns, 0.5 mL; Catalog # 87777 c) Suitable analytical balance d) Automatic pipette e) Class A volumetric glassware f) HPLC vials and caps g) Spatula and weigh boat h) Agilent 1290 Infinity II UHPLC System i) Agilent 6545XT AdvanceBio Quadrupole Time of Flight Mass Spectrometer (Q-ToF)

Example 2

Solution Preparation 2.1 Preparation of 100 mM Ammonium Bicarbonate 0.395±0.01 grams of ammonium bicarbonate was weighed in a 50 mL Falcon® tube. Using a measuring cylinder, 50 mL of LCMS water was transferred to the tube, and a vortex mixer was used to thoroughly dissolve ammonium bicarbonate to obtain 100 mM ammonium bicarbonate solution. The solution is stable for one month at 2-8° C.

2.2 Preparation of the First Mobile Phase (0.1% Trifluoroacetic Acid in Water)

Using a measuring cylinder, 1 L of LCMS water was transferred to a 1 L bottle. Using a pipette, 1000 μL of trifluoroacetic acid was transferred to the bottle. Trifluoroacetic acid and water were mixed well for 5 minutes to obtain the first mobile phase. The first mobile phase is stable for up to one month at ambient conditions.

2.3 Preparation of the Second Mobile Phase (0.1% Trifluoroacetic Acid in 90% Acetonitrile, and 10% Water)

900 mL of acetonitrile was added to a 1 L measuring cylinder. LCMS water was added to the 1 L measuring cylinder to make 1 L solution. The solution was transferred to a 1 L bottle. Using a pipette, 1000 μL of trifluoroacetic Acid was transferred to the bottle. Trifluoroacetic acid and the solution were mixed well for 5 minutes to obtain the second mobile phase. The second mobile phase is stable for up to one month at ambient conditions.

Example 3

Sample Preparation

The bottom closure of the spin columns was removed and the cap of the spin columns was loosened. The columns were placed into a 2 mL collection tube and were centrifuged at 1500 X g for 1 minute. When using fixed angle rotors, a mark was placed on the side of the column where the compacted resin was slanted upward. Column was then placed in the centrifuge with the mark facing outward for all subsequent steps.

400 μL of the 100 mM ammonium bicarbonate solution was added to the column and the column was centrifuged at 1500×g for 1 minute. This step was repeated two more times, and after each step, the flow-through was discarded. The column was placed into a new 2 mL collection tube. 5μg of the sample was slowly applied to the top of the compacted resin bed and incubated for 2 minutes at room temperature. The column was centrifuged at 1500×g for 2 minutes and the polymer free sample was collected. The sample volume was then made up to 100 μL with 100 mM Ammonium Bicarbonate and then transferred into a HPLC vial.

Example 4

Characterization of the VP1, VP2 and VP3 capsid proteins in an AAV particle

This example describes the methods of determining the ratio of VP1, VP2 and VP3 capsid proteins in an AAV particle, and the masses of the VP1, VP2 and VP3 capsid proteins. Here, an AAV particle was denatured and separated to the VP1, VP2 and VP3 capsid proteins in liquid chromatography. The separated VP1, VP2 and VP3 capsid proteins were first subjected to UV to determine the ratio of VP1, VP2 and VP3 capsid proteins in the AAV particle, and then to mass spectrometry to obtain the mass of each of the VP1, VP2 and VP3 capsid proteins.

4.1 LC Operating Conditions

The AAV VP1, VP2 and VP3 capsid proteins separations were performed on an ACQUITY UPLC® system using an ACQUITY UPLC® BEH 1.7 μm, 2.1×100 mm, C8 analytical column (Part no. 186002878). Mobile phases used were:

First mobile phase (A): 0.1% trifluoroacetic acid in water; and

Second mobile phase (B): 0.1% trifluoroacetic acid in 90% acetonitrile and 10% water.

The column temperature was maintained at about 80° C., and separation was achieved by using mobile phase B increasing from 10% to 40%, and from 40% to 45% at a flow rate of 0.4 mL/minute, followed by flushing with 100% mobile phase B for 1 minute and re-equilibrating with the starting mobile phase composition (10% mobile phase B) for another five minutes.

The LC operation conditions are listed in Table 2.

TABLE 2

| LC Operation Conditions | |
|---|---|
| Parameter | Setting |
| Mobile Phase A | 0.1% Trifluoroacetic Acid in water |
| Mobile Phase B | 0.1% Trifluoroacetic Acid in 90% Acetonitrile |
| Flow Rate | 0.4 mL/minute |
| Column | Waters ACQUITY UPLC BEH C8 Column, 2.1 × 100 mm, 1.7 μm; Part no. 186002878 |
| Column Temperature | 80° C. |
| Autosampler Temperature | 5° C. |
| Injector Volume | 100 μL |
| Detector Wavelength | 280 nm |
| Acquisition Time | 37 minutes |
| Post time | 5 minutes |

| Gradient Program | Time (minutes) | % A | % B |
|---|---|---|---|
| | 0.0 | 90 | 10 |
| | 3.0 | 90 | 10 |
| | 6.0 | 60 | 40 |
| | 35.0 | 55 | 45 |
| | 36.0 | 0 | 100 |
| | 37.0 | 90 | 10 |

4.2 Mass Spectrometer (MS) Operating Conditions

Mass spectroscopy were performed using Agilent 6545XT AdvanceBio Quadrupole Time of Flight Mass Spectrometer (Q-ToF), using API-ES ionization in a survey scan in the range of m/z values 700-13700 m/z. The capillary voltage, nozzle voltage, fragmentor voltage, and skimmer voltage were set at 5 kV, 500 V, 175 V, and 65 V, respectively. The drying gas temperature and drying gas flow were set at 300° C. and 13 L/min, respectively.

The mass spectrometer operating conditions are listed in Table 3.

TABLE 3

| Mass Spectrometer (MS) Operating Conditions | |
|---|---|
| Parameter | Setting |
| Ionization Mode | API-ES |
| Mass Range | 700-13700 m/z |
| Scan Type | Positive polarity |
| Data Acquisition Time | 17-28 minutes |
| Capillary Voltage | 5000 V |
| Nozzle Voltage | 500 V |
| Fragmentor | 175 V |
| Skimmer | 65 V |

TABLE 3-continued

| Mass Spectrometer (MS) Operating Conditions | |
| --- | --- |
| Parameter | Setting |
| OctopoleRFPeak | 750 |
| Nebulizer Pressure | 40 psig |
| Drying Gas Temperature | 300° C. |
| Drying Gas Flow | 13 L/min |
| Sheath Gas Temperature | 275° C. |
| Sheath Gas Flow | 12 L/min |
| MS Scan Rate | 0.50 spectra/second |
| Data Storage | Profile and Centroid |

Note:

MS parameters are for the Agilent 6545XT QToF and may need to be modified depending on the instrument used.

4.3 Analysis and Results

The capsid proteins were first denatured by heating the column compartment to 80° C. The three capsid proteins VP1, VP2 and VP3 were then baseline separated by using the Waters UPLC BEH C8 column (Part no. 186002878), eluted by the combination of a first mobile phase including 0.1% trifluoroacetic acid in water and a second mobile phase including 0.1% trifluoroacetic acid in the mixture of acetonitrile and water, wherein the percentage of the second mobile phase increases over time. The use of 0.1% trifluoroacetic acid as an ion-pairing agent in the mobile phases helps the baseline resolution.

The VP1, VP2 and VP3 capsid proteins separated in the liquid chromatography were first subjected to UV to determine the relative amounts and then to mass spectrometry to determine the masses of the VP1, VP2 and VP3 capsid proteins. The stoichiometry around 1:1:10 for VP1/VP2/VP3 was obtained by baseline integration of the UV chromatogram as shown in FIG. 1 and Table 4.

TABLE 4

| AAVrh74 Sample | VP1 | VP2 | VP3 |
| --- | --- | --- | --- |
| Sample 1 | 1.0 | 0.9 | 9.5 |
| Sample 2 | 1.0 | 1.7 | 7.9 |
| Sample 3 | 1.0 | 1.4 | 9.7 |

Peaks for the three capsid proteins were then deconvoluted using the parameters listed in Table 5. The total ion chromatogram, and deconvoluted spectra for all three peaks are shown in FIG. 2 and FIGS. 3A-3C. The three major masses detected under the VP1 peak (Theoretical Mass 81587 Da) were 81496 Da, 81578 Da and 81658 Da. The 81496 Da peak represents the VP1 protein with a loss of the N-terminal methionine and single acetylation modification. The other two peaks with a mass shift of +80 Da represents phosphorylation. Deconvolution of the VP2 peak (Theoretical Mass 66381 Da) showed two major masses: 66282 Da and 66360 Da. The 66282 Da peak represents the VP2 protein with a loss of threonine and the 66360 Da peak matches a single phosphorylation with a mass shift of +80. The VP3 peak (theoretical mass 59750 Da) showed a single major mass of 59662 Da which matches the mass of the VP3 protein with a loss of the N-terminal methionine and a single acetylation.

TABLE 5

| Deconvolution Parameters | |
| --- | --- |
| Parameter | Setting |
| Deconvolution Algorithm | Maximum Entropy |
| Mass Range | 45000-90000 Daltons |
| Mass Step | 0.1 Daltons |
| m/z Range | 700.00-3000.00 |
| Baseline Subtraction Factor | 7.00 |
| Isotope Width | Automatic |
| Peak Signal to Noise | 30.0 |
| Maximum Number of Peaks | 100 |
| Calculate Average Mass | 90% of Peak Height |
| Minimum Consecutive | 5 |
| Minimum Protein Fit Score | 8 |

FIG. 3 shows detection of post-translation modification of VP1, VP2, and VP3. Table 6 shows the intact mass analysis of AAV.rh74 capsid proteins.

TABLE 6

| Mass Analysis | | | |
| --- | --- | --- | --- |
| Capsid Protein | Theoretical Mass (Da) | Mass Observed (Da) | Species Identification |
| VP1 | 81586.4 | 81499.4 | Loss of Methionine plus Acetylation |
| | | 81579.0 | Loss of Methionine plus Acetylation and 1X Phosphorylation |
| | | 81660.6 | Loss of Methionine plus Acetylation and 2X Phosphorylation |
| VP2 | 66380.5 | 66280.9 | Loss of Threonine |
| | | 66360.7 | Loss of Threonine and 1X Phosphorylation |
| VP3 | 59750.2 | 59663.3 | Loss of Methionine plus Acetylation |

Example 5

Characterization of Deamidation of AAVrh74 using LCMS

Extensive deamidation in capsid proteins can be was determined by Mass Spectrometry, with which the sites of deamidation in the capsid proteins and also the levels of deamidation at these sites can be determined. To measure the AAV capsid deamidation, the capsid proteins were denatured and reduced at 90° C. for 10 minutes in the presence of 2M Guanidine Hydrochloride and 10 mM DTT. After cooling down the samples to room temperature, 30 mM Iodoacetamide was added for alkylation and incubated in dark at room temperature for 30 minutes. Alkylation was then quenched by addition of 1 mL of DTT. 20 mM Ammonium Bicarbonate was added to the samples to dilute down the Guanidine Hydrochloride to 200 mM. Samples were then digested using Trypsin in a 1:20 Enzyme:Protein ratio and incubated overnight at 37° C. After overnight incubation the digestion was quenched by adding to Trifluoroacetic Acid to a final concentration of 0.5% and the samples were analyzed on Thermo UltiMate 3000 RSLC system coupled to a Q Exactive HF with a NanoFlex source.

Table 7 shows major deamidation sites identified and the levels of deamidation (i.e., deamidation percentage) at these sites. The data for AAV8 in Table 7 is disclosed from a prior publication (Molecular Therapy, Volume 26 No 12, Pages 2848 — 2962 (2018)).

TABLE 7

| | | | Deamidation analysis results for AAV capsids | | |
|---|---|---|---|---|---|
| Peptide Sequence | Sequence Location in VP1 | Amino Acid Residue | AAV8 (Ammonium Bicarbonate as buffer) | AAVrh74 (Ammonium Bicarbonate as buffer) | AAVrh74 (Tris HCl as buffer) |
| QISNGTSGGSTNDNT YFGYSTPWGYFDFNR (SEQ ID NO: 1) | A (260-289) | N263 | 100 | 89 | ND |
| YHLNGR (SEQ ID NO: 2) | A (511-516) | N514 | 92 | 94 | 22 |
| YLGPFNGLDK (SEQ ID NO: 3) | A (52-61) | N57 | 67 | 74 | 26 |
| VSTTLSQNNNSNF AWTGATK (SEQ ID NO: 4) | A (491-510) | N502 | 66 | 36 | 3 |
| TWALPTYNNHLYK (SEQ ID NO: 5) | A (247-259) | N254 | 21 | 24 | 2 |
| YNHADAEFQER (SEQ ID NO: 6) | A (93-103) | N94 | 11 | 12 | ND |

Two buffers (ammonium bicarbonate and Tris-HCl) were used separately to measure the deamidation status of AAV.rh74.

For ammonium bicarbonate, samples were denatured by performing a buffer exchange into 100 mM Ammonium Bicarbonate. The denatured samples were reduced by addition of 10 mM DTT and incubated at 37° C. for 45 minutes. Alkylation was then performed by addition of Iodoacetamide in the samples to a final concentration of 30 mM. The denatured, reduced and alkylated samples were then exchanged back into 100 mM Ammonium Bicarbonate using a 10 kDa Amicon Ultra filter. Samples were then digested using Trypsin and incubated overnight at 37° C. Using this sample preparation in which the digestion was performed in Ammonium Bicarbonate, similar levels of deamidation were obtained for AAVrh74 as seen in Table 7.

For Tris-HCl, a 60 μg sample aliquot was buffer-exchanged into 4 M guanidine and 200 mM Tris pH 7.5 using an Amicon 10 K centrifugal filter to remove the sample matrix and concentrate the protein. The guanidine concentration was adjusted to 6 M and DTT (10 mM) was added to the 60 μg aliquot. The reaction mixture was incubated at 56° C. for 45 minutes, then cooled to room temperature. Iodoacetamide (30 mM) was added, with incubation at room temperature in the dark for 60 minutes. Tris buffer (100 mM, pH=7.5) was then added to dilute the guanidine HCl concentration to 0.6 M. Trypsin/Lys-C (60 μg) was added to 60 μg of the reduced and alkylated sample (enzyme:protein ratio —1:1 (w:w)). Methionine was added to 10 mM in the digestion to minimize artefactual oxidations. The digestion was carried out overnight (17 hours) at 37° C. TFA (1%) was then added prior to LC-MS/MS analysis.

As shown in Table 7, with Tris-HCl as buffer, the deamidation status was significantly lower as compared to those with Ammonium Bicarbonate.

Figure 4:
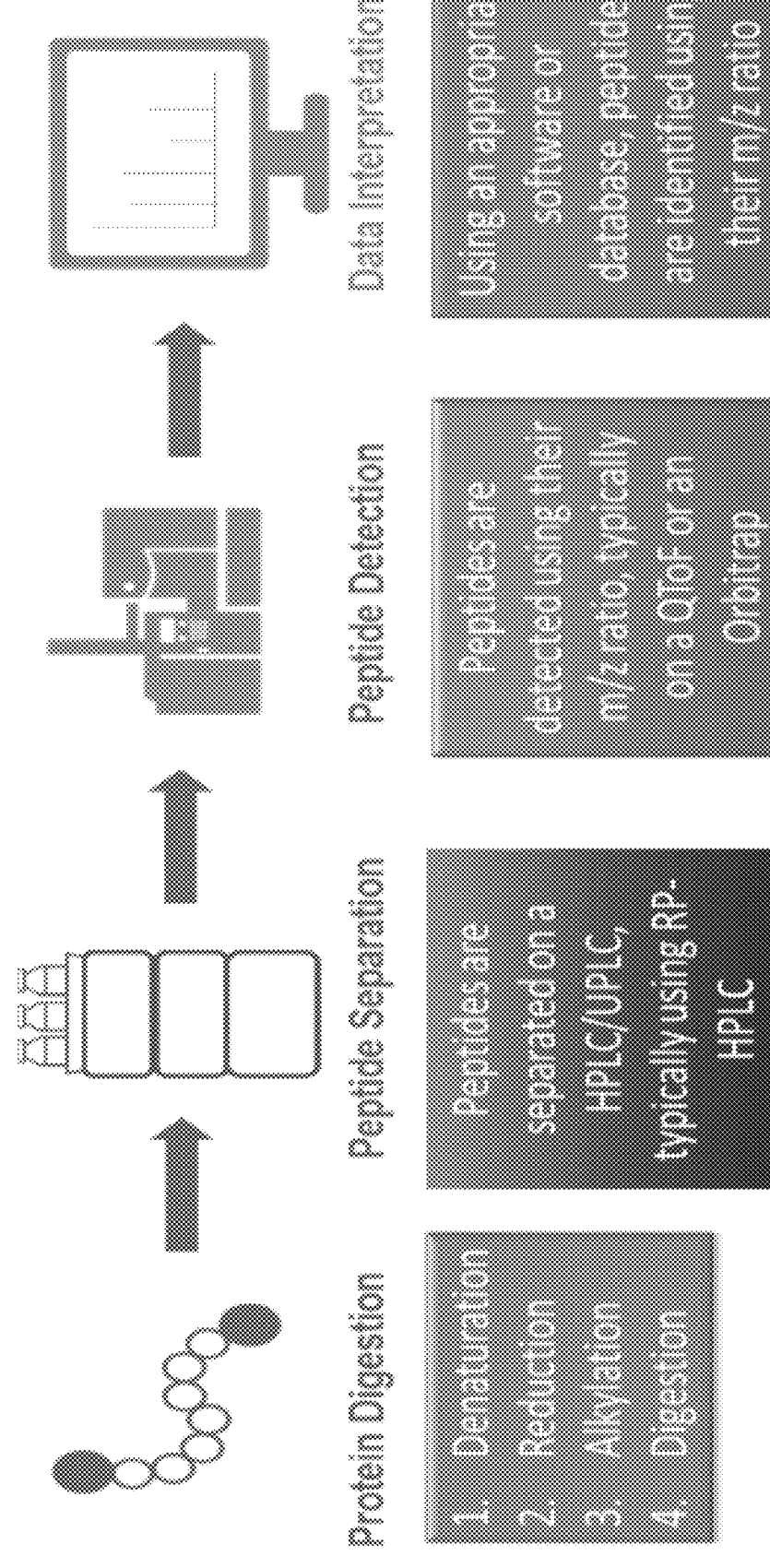
FIG. 4 shows the process of deamidation analysis with Tris-HC1 as the buffer.

To further optimize the methods with Tris-HCl, eight separate AAV capsid samples were measured according to the flow chart in FIG. 4. The samples were first denatured by performing a buffer exchange into 6M Guanidine Hydrochloride, 20 mM Tris-HCl, pH 7.5. Samples were then reduced by adding DTT to a final concentration of 10 mM and incubated at 37° C. for 45 minutes. Alkylation was performed by adding Iodoacetamide to a final concentration of 30 mM and incubated in the dark at room temperature for 1 hour. The samples were again buffer exchanged into 20 mM Tris-HCl, pH 7.5 using 10 kDa Amicon Ultra filters. Acetonitrile was then added to the samples to a final concentration of 10% and Methionine was also added to a final concentration of 10 mM. Samples were digested overnight at 37° C. using Trypsin. Peptides are then separated on an Agilent 1290 U-HPLC using RP-HPLC. The separated peptides are then detected using an Agilent 6545XT QToF and deamidation analysis is performed using the Mass-Hunter and Bioconfirm softwares. The deamidation status is shown in FIG. 5, and the oxidation status is shown in FIG. 6. Out of the 52 Asparagine residues present, no deamidation was observed at 48 residues (Total Asparagine residues in VP1: 56). Out of the 39 Glutamine residues present, no deamidation was observed at all 39 residues (Total Glutamine residues in VP1: 48). Using O18 Labeled water a small amount of the deamidation at N57 was shown to be a sample preparation related artifact. No Oxidation was detected at the 5 remaining Methionine residues (Total Methionine residues in VP1: 11). Out of the 14 Tryptophan residues detected, no oxidation was observed at all 14 residues (Total Tryptophan residues in VP1: 15).

Digestion in Ammonium Bicarbonate can increase deamidation artifacts significantly due to the increase in the pH over time. Therefore, the higher levels of deamidation observed could be deamidation artifacts generated during sample preparation. Tris HCl based digestion was set up at Sarepta to confirm the deamidation levels: 20 mM Tris HCl, pH 7.5 was used as the buffer; 10% Acetonitrile was added to the digestion solution as it is known to reduce deamidation artifacts; and 10 mM Methionine was also added to the digestion solution to reduce the oxidation artifacts Therefore, the method of this disclosure is more accurate in measuring deamidation, oxidation, or other post-translation modification with the Tris-HCl buffer.

Example 6

Characterization of Host Cell Proteins Using LC-QTOF-MS

The purity of a rAAV based gene therapy drug product was analyzed by characterizing the host cell proteins remaining in the AAV composition through LC-QTOF-MS.

6.1 Preparation of Sample

An AAVrh74 sample was spiked with a known amount of human thioredoxin 1 (HTI) protein standard, Invitrogen, (Catalog No. LF-P0001) and bovine carbonic anhydrase II (BCAII) protein standard, Sigma, (Catalog No. C7749). Human Thioredoxin 1 (HTI) and bovine carbonic anhydrase II (BCAII) were selected as the spiking protein standards for quantitate human and bovine HCPs found, respectively. For immune-depletion process, pipette 100 µL of 0.05 mg/mL Anti-Adeno-associated virus (AAV), VP1/VP2/VP3 antibody, and 100 µL of the sample solution, along with 20 µL of 0.05 mg/mL BCAII and 10 µL of 0.1 mg/mL HTI into 270 µl of IP-MS cell lysis buffer from Pierce MS-compatible magnetic IP kit. AAV capsid proteins were then immuno-precipitated from the sample with anti-adeno-associated virus (AAV), VP1/VP2/VP3 from American Research Products, Inc. (Catalog # 03-6105) and the Pierce MS-compatible magnetic IP kit (Catalog # 90409). The sample was then passed through the Pierce detergent removal spin columns (Catalog # 87777).

The samples were then buffer exchanged into Promega rapid digestion buffer (Catalog # VA1060). The samples were reduced, alkylated, and digested with rapid digestion trypsin at 70° C. for 60-180 minutes.

6.2 LC Operating Conditions

Digested residual host cell protein separation was performed on an Agilent 1290 HPLC system using a Waters Acquity peptide BEH C18, 1.7 µm, 2.1×150 mm column. Mobile phases used are:

First mobile phase (A): 0.1% formic acid in water; and

Second mobile phase (B): 0.1% formic acid in 90% acetonitrile and 10% water.

The column temperature was maintained at about 45° C., and separation was achieved by using mobile phase B increased from 2% to 50%, and from 50% to 100% at a flow rate of 0.3 mL/minute, followed by flushing with 100% mobile phase B for 3 minutes and re-equilibrating with the starting mobile phase composition (2% mobile phase B) for another 5 minutes.

The LC operation conditions are listed in Table 8.

TABLE 8

LC Operation Conditions

| Parameter | Setting |
| --- | --- |
| Mobile Phase A | 0.1% Formic Acid in water |
| Mobile Phase B | 0.1% Formic Acid in 90% Acetonitrile |
| Flow Rate | 0.3 mL/minute |
| Column | Waters ACQUITY peptide BEH C8 Column, 2.1 × 150 mm, 1.7 µm; |
| Column Temperature | 45° C. |
| Autosampler Temperature | 4° C. |
| Injector Volume | 100 µL |
| Needle Wash | 50% Acetonitrile/50% water |
| Acquisition Time | 130 minutes |
| Post time | 5 minutes |

TABLE 8-continued

LC Operation Conditions

| Gradient Program | Time (minutes) | % A | % B |
| --- | --- | --- | --- |
| | 0.0 | 98 | 2 |
| | 115.0 | 50 | 50 |
| | 120.0 | 0 | 100 |
| | 123.0 | 0 | 100 |
| | 125.0 | 98 | 2 |

6.3 Mass Spectrometer (MS) Operating Conditions

Mass spectroscopy was performed using Agilent 6545XT AdvanceBio Quadrupole Time of Flight Mass Spectrometer (Q-ToF), using API-ES ionization in a survey scan in the range of m/z values 50-3000 m/z. The capillary voltage, nozzle voltage, fragmentor voltage, and skimmer voltage were set at 4 kV, 500 V, 135 V, and 65 V, respectively. The drying gas temperature and drying gas flow were set at 325° C. and 12 L/min, respectively.

The mass spectrometer operating conditions are listed in Table 9.

TABLE 9

Mass Spectrometer (MS) Operating Conditions

| Parameter | Setting | | |
| --- | --- | --- | --- |
| Gas Temperature | 325° C. | | |
| Dry Gas | 12 L/min | | |
| Nebulizer | 35 psig | | |
| Sheath Gas Temperature | 275° C. | | |
| Sheath Gas | 12 L/min | | |
| Vcap | 4000 V | | |
| Nozzle voltage | 500 V | | |
| Fragmentor | 135 V | | |
| Skimmer | 65 V | | |
| Oct 1 RF vpp | 750 V | | |
| MS acquisition | 300 to 3000 m/z | | |
| MS/MS acquisition | 50 to 3000 m/z | | |
| MS storage threshold | 400 absolute/0.01% relative threshold | | |
| MS/MS storage threshold | 5 absolute/0.02% relative threshold | | |
| Auto MS/MS acquisition rate | | | |
| MS | 3 spectra/s | | |
| MS/MS | 2 spectra/s | | |
| Isolation width | Narrow | | |
| Collision Energy | Charge | Slope | Offset |
| | 2 | 3.1 | 1 |
| | 3 | 3.6 | −4.8 |
| | >3 | 3.6 | −4.8 |
| Precursor selection I | 6 max precursor per cycle | | |
| Absolute threshold | 2000 counts | | |
| Relative threshold | 0.001% | | |
| Active exclusion | Enabled, excluded after 1 spectra, release after 0.15 min | | |
| Iterative MS/MS | Use PC for MS/MS | | |
| Mass error tolerance | ±20 ppm | | |
| RT exclusion tolerance | ±0.3 min | | |
| Isotope model | Peptides | | |
| Precursor charge state selection | 2, 3, >3 | | |
| Abundance dependent accumulation | Scan speed varied based on precursor abundance | | |
| Target | 45000 counts/spectrum | | |
| | Use MS/MS accumulation time limit | | |
| Purity Stringency | 100% | | |
| Purity Cutoff | 30% | | |
| Reference Mass | 322 and 2422 | | |
| Detection Window | 500 ppm | | |
| Minimum height | 400 counts | | |
| Time segments | 0 to 2 min to waste | | |
| | 2 to 120 min to MS | | |
| | 120 to 130 min to waste | | |

6.4 Analysis and Results

The data generated in Example 6.3 were processed by Byos software from Protein Metrics to search against certain Uniprot protein database. The identity and relative quantity of each residual protein were calculated against the amount of the amount of spiked protein standards. HCP analysis indicated that only few residual host cell proteins (two bovine proteins, but no human proteins) were identified by MS for three lots of AAV viral particles (Table 10). The concentrations for the proteins are in the order of ng/mL, or ppm level based on the spiked protein standards.

TABLE 10

| | | | | | | three lots of Host Cell Protein analyzed by LC/MS | | |
|---|---|---|---|---|---|---|---|---|
| Protein | Uniprot ID | Protein Identified | Species | Size (kDa) | Peptide coverage (%) | B634-0220-002 | NCH G02B1117 | NCH G22A0219 |
| 1 | O46375 | Transthyretin | Bovine | 16 | 61.9 | 2.0 ng/mL | 0.0 ng/mL | 14.0 ng/mL |
| 2 | Q3SZR3 | Alpha-1-acid glycoprotein | Bovine | 23 | 39.1 | 133.0 ng/mL | 27.0 ng/mL | 69.0 ng/mL |

The following references are incorporated herein in their entirety:

1. Buller R M, Rose J A. Characterization of adenovirus-associated virus-induced polypeptides in K B cells. J Virol 25: 1978, Pages 331-338.
2. Johnson FB, Ozer H L, Hoggan M D. Structural proteins of adenovirus-associated viruses. J Virol 8:1971, Pages 776-770.
3. D. W. Bauer. et.al. Exploring the Balance between DNA Pressure and Capsid Stability in Herpesviruses and Phages. J Virol 2015, 9288-98.
4. Vamseedhar Rayaprolu.et.al. Comparative Analysis of Adeno-Associated Virus Capsid Stability and Dynamics. J Virol 2013, 13150-60.
5. Xiaoying Jin et.al. Direct Liquid Chromatography/ Mass Spectrometry Analysis for Complete Characterization of Recombinant Adeno-Associated Virus Capsid Proteins. Human Gene Therapy Methods, Volume 38 Number 5 2017, 255-267.

---

We claim:

1. A method of characterizing capsid viral protein 1 (VP1), capsid viral protein 2 (VP2), and capsid viral protein 3 (VP3) in an adeno-associated virus (AAV) particle using a reverse liquid chromatography column having a stationary phase and an ultraviolet (UV)-visible spectrometer, the method comprising:

(a) subjecting the AAV particle to the reverse phase liquid chromatography column, wherein the subjecting comprises:

(a1) introducing the AAV particle into the reverse phase liquid chromatography column, (a2) maintaining the reverse phase liquid chromatography column at a temperature approximately between 70° C. and 90° C., (a3) contacting the AAV particle with a first mobile phase having a trifluoracetic acid volume percentage approximately between 0.05% and 0.15%, and (a4) eluting VP1, VP2, and VP3 from the reverse phase liquid chromatography to produce corresponding VP1, VP2, and VP3 capsid viral protein chromatographic peaks;

(b) detecting the corresponding VP1, VP2, and VP3 capsid viral protein chromatographic peaks using the ultraviolet (UV)-visible spectrometer; and (c) determining corresponding relative abundances of VP1, VP2, and VP3 capsid protein based on the detected corresponding VP1, VP2, and VP3 capsid viral protein chromatographic peaks.

2. The method of claim 1, further comprising determining VP1 mass, VP2 mass, and VP3 mass using a mass spectrometer.

3. The method of claim 1, wherein the determining comprises comparing a VP1 ultraviolet chromatogram with a VP2 ultraviolet chromatogram and with a VP3 ultraviolet chromatograph and comparing the VP2 ultraviolet chromatogram with the VP3 ultraviolet chromatograph.

4. The method of claim 1, wherein the stationary phase comprises a plurality of silica particles bonded to hydrocarbon chains having 18, 8, or 4 carbon atoms.

5. The method of claim 4, wherein the plurality of silica particles have a size between about 1.2 μm and about 3.5 μm.

6. The method of claim 4, wherein the reverse phase liquid chromatography column has a length between about 50 mm and about 300 mm long and has an internal diameter between about 1 mm and about 4.6 mm.

7. The method of claim 1, wherein the AAV particle is of AAV1, AAV2, AAV3, AAV4, AAV5, AAV6, AAV7, AAV8, AAV9, AAV10, AAV 11, AAV12, AAV13, AAVrh10, AAVrh74 serotype.

8. The method of claim 1, wherein the contacting comprises introducing the first mobile phase into the reverse phase liquid chromatography column at a first flow rate and a second mobile phase at a second flow rate, wherein the second mobile phase comprises a mixture of trifluoroacetic acid, acetonitrile, and water.

9. The method of claim 8, wherein the second mobile phase comprises an acetonitrile volume percentage between about 80% and 95%.

10. The method of claim 8, wherein the contacting further comprises increasing the second flow rate relative to the first flow rate.

11. The method of claim 1, further comprising determining one or more post translational modifications in VP1, VP2, or VP3, or a combination thereof.

12. The method of claim 11, wherein the one or more post translational modifications comprises loss of an amino acid, glycosylation, sialylation, acetylation, phosphorylation, deamidation, oxidation, formylation, hydroxylation, methylation, or sulfation, or a combination thereof.

13. The method of claim 11, wherein the first mobile phase further comprises Tris-HC1.

14. The method of claim 13, wherein the first mobile phase further comprises acetonitrile.

15. The method of claim 13, wherein the first mobile phase further comprises methionine.

16. The method of claim 13, wherein the first mobile phase has a formulation comprising a Tris-HC1 molar concentration approximately between 5 mM and 50 mM, an acetonitrile volume percent between approximately 5% and 20%, and a methionine molar concentration between approximately 1 mM and 50 mM.

17. The method of claim 11, wherein the one or more post translational modifications comprise one or more deamidation sites at N263, N514, N57, N502, N254, and N94 of AAV8 or a combination thereof, or an equivalent residue of AAV1, AAV2, AAV3, AAV4, AAV5, AAV6, AAV7, AAV9, AAV10, AAV11, AAV12, AAV 13 AAV13, AAVrh10, or AAVrh74.

\* \* \* \* \*

SEQUENCE LISTING

```
<160> NUMBER OF SEQ ID NOS: 6

<210> SEQ ID NO 1
<211> LENGTH: 30
<212> TYPE: PRT
<213> ORGANISM: Artificial Sequence
<220> FEATURE:
<223> OTHER INFORMATION: AAV capsid peptide sequence

<400> SEQUENCE: 1

Gln Ile Ser Asn Gly Thr Ser Gly Gly Ser Thr Asn Asp Asn Thr Tyr
1               5                   10                  15

Phe Gly Tyr Ser Thr Pro Trp Gly Tyr Phe Asp Phe Asn Arg
            20                  25                  30

<210> SEQ ID NO 2
<211> LENGTH: 6
<212> TYPE: PRT
<213> ORGANISM: Artificial Sequence
<220> FEATURE:
<223> OTHER INFORMATION: AAV capsid peptide sequence

<400> SEQUENCE: 2

Tyr His Leu Asn Gly Arg
1               5

<210> SEQ ID NO 3
<211> LENGTH: 10
<212> TYPE: PRT
<213> ORGANISM: Artificial Sequence
<220> FEATURE:
<223> OTHER INFORMATION: AAV capsid peptide sequence
```

-continued

```
<400> SEQUENCE: 3

Tyr Leu Gly Pro Phe Asn Gly Leu Asp Lys
1               5                   10

<210> SEQ ID NO 4
<211> LENGTH: 20
<212> TYPE: PRT
<213> ORGANISM: Artificial Sequence
<220> FEATURE:
<223> OTHER INFORMATION: AAV capsid peptide sequence

<400> SEQUENCE: 4

Val Ser Thr Thr Leu Ser Gln Asn Asn Asn Ser Asn Phe Ala Trp Thr
1               5                   10                  15

Gly Ala Thr Lys
            20

<210> SEQ ID NO 5
<211> LENGTH: 13
<212> TYPE: PRT
<213> ORGANISM: Artificial Sequence
<220> FEATURE:
<223> OTHER INFORMATION: AAV capsid peptide sequence

<400> SEQUENCE: 5

Thr Trp Ala Leu Pro Thr Tyr Asn Asn His Leu Tyr Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: AAV capsid peptide sequence

<400> SEQUENCE: 6

Tyr Asn His Ala Asp Ala Glu Phe Gln Glu Arg
1               5                   10
```